United States Patent
Kaufman

(10) Patent No.: US 8,114,596 B2
(45) Date of Patent: *Feb. 14, 2012

(54) PRODUCING, CATALOGING AND CLASSIFYING SEQUENCE TAGS

(76) Inventor: Joseph C. Kaufman, Hamden, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/576,287

(22) Filed: Oct. 9, 2009

(65) Prior Publication Data
US 2010/0055745 A1 Mar. 4, 2010

(51) Int. Cl.
*C12Q 1/68* (2006.01)
*C12P 19/34* (2006.01)
*C07H 21/02* (2006.01)
*C07H 21/04* (2006.01)

(52) U.S. Cl. ...... 435/6.1; 435/6.11; 435/6.12; 435/91.2; 435/91.52; 536/23.1; 536/24.3

(58) Field of Classification Search .......... 435/6.1, 435/6.11, 6.12, 91.2, 91.52; 536/23.1, 24.2
See application file for complete search history.

(56) References Cited

U.S. PATENT DOCUMENTS

| | | | |
|---|---|---|---|
| 5,124,246 A | 6/1992 | Urdea et al. | |
| 5,624,802 A | 4/1997 | Urdea et al. | |
| 5,677,153 A | 10/1997 | Botstein et al. | |
| 5,710,264 A | 1/1998 | Urdea et al. | |
| 5,770,365 A | 6/1998 | Lane et al. | |
| 5,780,233 A | 7/1998 | Guo et al. | |
| 5,849,481 A | 12/1998 | Urdea et al. | |
| 6,027,894 A | 2/2000 | Sapolsky et al. | 435/6 |
| 6,045,994 A | 4/2000 | Zabeau et al. | |
| 6,054,276 A | 4/2000 | Macevicz | |
| 6,057,100 A | 5/2000 | Heyneker | |
| 6,261,782 B1 | 7/2001 | Lizardi et al. | |
| 6,268,147 B1 | 7/2001 | Beattie et al. | |
| 6,319,426 B1 | 11/2001 | Bawendi et al. | |
| 6,383,754 B1 | 5/2002 | Kaufman et al. | |
| 6,406,856 B1 | 6/2002 | Glover et al. | |
| 6,497,895 B2 | 12/2002 | Uhrich | |
| 6,521,736 B2 | 2/2003 | Watterson et al. | |
| 6,540,981 B2 | 4/2003 | Klaveness et al. | |
| 6,671,625 B1 | 12/2003 | Gulati | |
| 6,677,121 B2 | 1/2004 | Lizardi et al. | |
| 6,689,391 B2 | 2/2004 | Goswami et al. | |
| 6,699,499 B1 | 3/2004 | Aneja | |
| 6,699,975 B2 | 3/2004 | Reed et al. | |
| 6,730,334 B2 | 5/2004 | Zhao | |
| 6,734,296 B1 | 5/2004 | Grossman | |
| 6,824,981 B2 | 11/2004 | Chait et al. | |
| 6,872,450 B2 | 3/2005 | Liu et al. | |
| 6,884,842 B2 | 4/2005 | Soane et al. | |
| 2003/0045694 A1 | 3/2003 | Chait et al. | |
| 2003/0082556 A1 | 5/2003 | Kaufman et al. | |
| 2003/0096239 A1 | 5/2003 | Gunderson et al. | |
| 2003/0108897 A1 | 6/2003 | Drmanac | |
| 2004/0009506 A1 | 1/2004 | Stephen et al. | |
| 2004/0009584 A1 | 1/2004 | Mitra et al. | |
| 2004/0023261 A1 | 2/2004 | Bruchez et al. | |
| 2004/0058006 A1 | 3/2004 | Barry et al. | |
| 2004/0198641 A1 | 10/2004 | Uhrich et al. | |
| 2004/0241724 A1 | 12/2004 | Karlsson et al. | |
| 2004/0243645 A1 | 12/2004 | Broder et al. | |
| 2004/0248144 A1 | 12/2004 | Mir | |
| 2004/0265888 A1 | 12/2004 | Kaufman et al. | |
| 2005/0019901 A1 | 1/2005 | Matveeva et al. | |
| 2005/0042623 A1 | 2/2005 | Ault-Riche et al. | |
| 2005/0059137 A1 | 3/2005 | Lee | |
| 2005/0064446 A1 | 3/2005 | Bamdad et al. | |
| 2005/0074774 A1 | 4/2005 | Woudenberg et al. | |
| 2005/0074898 A1 | 4/2005 | Datwani et al. | |

(Continued)

FOREIGN PATENT DOCUMENTS
WO    9919276 A2    4/1999
(Continued)

OTHER PUBLICATIONS

International Search Report for PCT/US2005/019715. Mailed Jan. 19, 2006.
Written Opinion of the International Searching Authority for PCT/US2005/019715. Mailed Jan. 19, 2006.
Kato, Kikuya., "Description of the entire mRNA population by a 3' end cDNA fragment generated by class IIS restriction enzymes". Nucleic Acids Research, 1995, vol. 23, No. 18 pp. 3685-3690.
Albert, Thomas J. et al., "Light-directed 5'-3' synthesis of complex oligonucleotide microarrays", *Nucleic Acids Research*, (2003) 31(7): 1-9.
Angelov, Stanislav et al., "Genome Identification and Classification by Short Oligo Arrays", *Lecture Notes in Computer Science*, vol. 3240, Jan. 2004, pp. 400-411.

(Continued)

*Primary Examiner* — Stephen Kapushoc
*Assistant Examiner* — Narayan Bhat
(74) *Attorney, Agent, or Firm* — Cantor Colburn LLP

(57) ABSTRACT

The described method provides, methods, and kits to produce, identify, catalog and classify a comprehensive collection of nucleic acid targets produced from a nucleic acid sample. The method, referred to as Cataloging and Classification of Sequence Tags, involves generating a set of target nucleic acid fragments; coupling the target nucleic acid fragments to a nucleic acid bridge comprising, for example, two or more primer binding sites and two recognition sites for cleavage at a site offset from the recognition site to the fragment's end; and cleaving the fragments to generate chimeric nucleic acids of known length. The nucleic acid bridge is thus disposed between the two nucleic acid fragments in the chimeric nucleic acid. The resulting duplex nucleic acids comprise a set of sequence tags (i.e., by amplification using universal primers), comprising an addressable portion, a target nucleic portion and a portion of the nucleic acid bridge. Single-stranded or partial duplex sequence tags may be captured by coupling to a complementary capture probe. Capture probe-sequence tag hybrids, may be detected employing a labeled detector probe. The method allows a complex sample of nucleic acids to be cataloged in a reproducible and sequence-specific manner. The method further provides methods for analysis of the above sample to classify the sequence tags; determine the presence and relative amounts of sequences of interest; derive expressed genes signatures and differential gene expression signatures; and identify putative expressed sequence tags (EST).

16 Claims, 19 Drawing Sheets

U.S. PATENT DOCUMENTS

Figure 1:
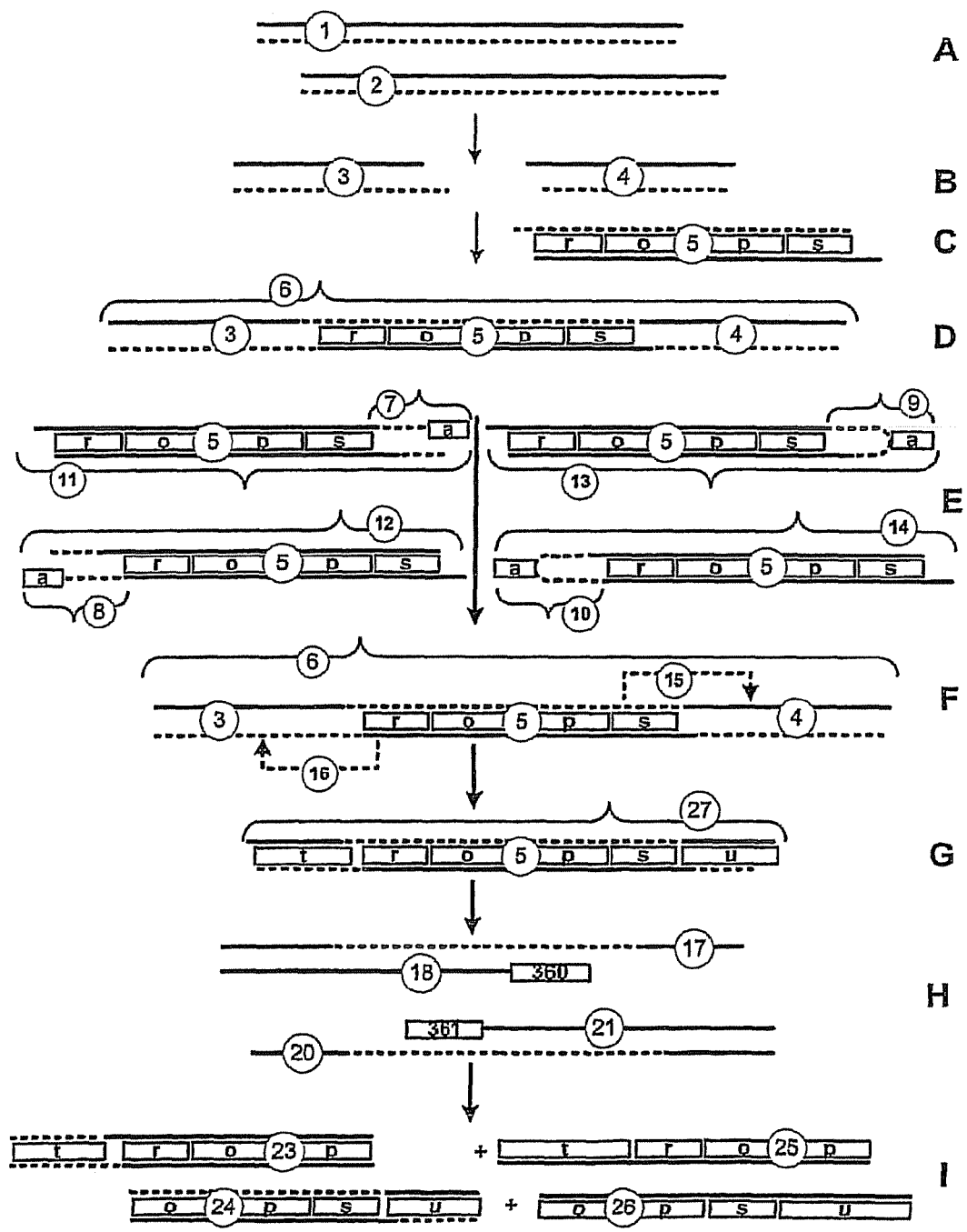

| | | | |
|---|---|---|---|
| 2005/0075859 A1 | 4/2005 | Ramsey | |
| 2005/0107478 A1 | 5/2005 | Klimov et al. | |

FOREIGN PATENT DOCUMENTS

| | | |
|---|---|---|
| WO | WO 00/60124 | 10/2000 |
| WO | WO 01/61036 A2 | 8/2001 |
| WO | WO 02/08464 A1 | 1/2002 |

OTHER PUBLICATIONS

Brenner, Sydney et al., "Gene expression analysis by massively parallel signature sequencing (MPSS) on microbead arrays", *Nature Biotechnology*, (2000) 18:630-634.

Broude, Natalia E. et al., "DNA microarrays with stem-loop DNA probes: preparation and applications", *Nucleic Acids Research*, (2001) 29(19):2-11.

Broude, Natalia E. et al., "Enhanced DNA sequencing by hybridization", *Proc. Natl. Acad. Sci. USA*, (1994) 91:3072-3076.

Bruchez, Marcel Jr., et al., "Semiconductor Nanocrystals as Fluorescent Biological Labels" *Science*, (1998) 281:2013-2016.

Burke, John et al., "d2_cluster: A Validated Method for Clustering EST and Full-Length cDNA Sequences" *Genome Research*, (1999) 9:1135-1142.

Callow, Matthew J. et al., "Selective DNA amplification from complex genomes using universal double-sided adapters", *Nucleic Acids Research*, (2004) 32(2):1-6.

Chandler, Darrell P., "Unshackling expression profiling arrays", *Nature Biotechnology*, (2004) 22(4):396-397.

Chou Shan-Ho, et al., "Unusual DNA duplex and hairpin motifs", Nucleic Acids Res. May 15, 2003;31(10):2461-74. Review.

Dirks Robert M., et al., "Triggered amplification by hybridization chain reaction", Proc. Natl. Acad. Sci., U S A, Oct. 26, 2004;101(43):15275-8. Epub Oct. 18, 2004.

Graff, Alexandra et al., "Virus-assisted loading of polymer nanocontainer", *Proc. Natl. Acad. Sci., USA*, (2002) 99(8):5064-5068.

Guilfoyle, Richard A. et al., "Ligation-mediated PCR amplification of specific fragments from a Class-II restriction endonuclease total digest" *Nucleic Acids Research*, (1997) 25(9):1854-1858.

Gunderson, Kevin L. et al., "Mutation Detection by Ligation to Complete n-mer DNA Arrays" *Genome Research*, (1998) 8:1142-1153.

Halford, S.E., "Hopping, jumping and looping by restriction enzymes", *Biochemical Society Transactions (2001)*, 29(4):363-373.

Hardiman, Gary, "Microarray platforms—comparisons and contrasts", *Pharmacogenomics*, (2004) 5(5):487-502.

Horejsh, Douglas et al., "A molecular beacon, bead-based assay for the detection of nucleic acids by flow cytometry", *Nucleic Acids Research*, (2005) 33(2):1-7.

Kuhn, Kenneth et al., "A novel, high-performance random array platform for quantitative gene expression profiling", *Genome Research*, (2004) 14:2347-2356.

Kreiner, Thane and Tillman Buck, Katie, "Moving toward whole-genome analysis: A technology perspective", *Am J Health-Syst Pharm*, (2005) 62:296-305.

Lane, Michael J. et al., "The thermodynamic advantage of DNA oligonucleotide 'stacking hybridization' reactions: energetics of a DNA nick", *Nucleic Acids Research*, (1997) 25(3):611-616.

Li Yougen, et al., "Multiplexed detection of pathogen DNA with DNA-based fluorescence nanobarcodes", Nat Biotechnol. Jul. 2005;23(7):885-9. Epub Jun. 12, 2005.

Li, Zengmin et al.,"A photocleavable fluorescent nucleotide for DNA sequencing and analysis", *Proc. Natl. Acad. Sci., USA*, (2003) 100(2):414-419.

Loakes, David, "Survey and summary: The applications of universal DNA base analogues", Nucleic Acids Res. Jun. 15, 2001;29(12):2437-47. Review.

Lukhtanov, Eugene A. et al., "Fluorogenic DNA probes for multicolor hybridization assays", *American Biotechnology Laboratory*, Sep. 2001:68-69.

Matsumura, Hideo et al., "Gene expression analysis of plant host-pathogen interactions by SuperSAGE", *Proc. Natl. Acad. Sci.*, (2003) 100(26):15718-15723.

Mayer, Günter and Jenne, Andreas, "Aptamers in Research and Drug Development", *Biodrugs*, (2004) 18(6):351-359.

Ouhib, Farid et al., "Polymeric Micelles and Nanoparticles from Block and Statistical Poly((RS)-3,3-dimethylmalic acid) Derivatives: Preparation and Characterization", *Macromolecular Bioscience*, (2005) 5:299-305.

Park, Jeong Won et al., "Preparation of Oligonucleotide Arrays with High-Density DNA Deposition and High Hybridization Efficiency", *Bull. Korean Chem. Soc.*, (2004) 25(11):1667-1670.

Petruska, Melissa A. et al., "An Amphiphilic Approach to Nanocrystal Quantum Dot-Titania Nanocomposites", *J. AM. Chem. Soc.*, (2004) 126:714-715.

Riccelli, P. V. et al., "Hybridization of single-stranded DNA targets to immobilized complementary DNA probes: comparison of hairpin versus linear capture probes", *Nucleic Acids Research*, (2001) 29(4):996-1004.

Riccelli, P.V. et al., "Melting studies of dangling-ended DNA hairpins: effects of end length, loop sequence and biotinylation of loop bases", *Nucleic Acids Research*, (2002) 30(18):4088-4093.

Rosario, Barbara and Hearst, Marti, "Classifying Semantic Relations in Bioscience Texts", *Proceedings of the Annual Meeting of Association of Computational Linguistics* (ACL '04), 2004.

Roth, Matthew E., et al., "Expression profiling using a hexamer-based universal microarray", *Nature Biotechnology*, (2004) 22(4):418-426.

Saiyed, Zm et al., "Application of magnetic techniques in the field of drug discovery and biomedicine", *BioMagnetic Research and Technology (2003)* 1:2 (www.biomagres.com/content/1/1/2).

SantaLucia John Jr., et al.,"The thermoynamics of DNA structural motifs", Annu Rev Biophys Biomol Struct. 2004;33:415-40. Review.

Schwartz, Frederick P. et al., "Thermodynamic comparison of PNA/DNA and DNA/DNA hybridization reactions at ambient temperature", *Nucleic Acids Research*, (1999) 27(24):4792-4800.

Tengs Torstein, et al., "Genomic representations using concatenates of Type IIB restriction endonuclease digestion fragments", Nucleic Acids Res. Aug. 25, 2004;32(15):e121.

Tian, Huan et al., "Multiplex mRNA Assay Using Electrophoretic Tags for High-Throughput Gene Expression Analysis", *Nucleic Acids Res.* Sep. 8, 2004:32 (16):e1-26.

Walker G. Terrance, et al., "Strand displacement amplification—an isothermal, in vitro DNA amplification technique", Nucleic Acids Res. Apr. 11, 1992;20(7):1691-6.

Wang, Jinke et al., "DNA microarrays with unimolecular hairpin double-stranded DNA probes: fabrication and exploration of sequence-specific DNA/protein interactions", *J. Biochemical and Biophysical Methods*, (2003) 55:215-232.

Wheeler, David L. et al., "Database resources of the National Center for Biotechnology Information", *Nucleic Acids Research*, (2005) 33:D39-D45.

Wu Chunlei, et al., "Sequence dependence of cross-hybridization on short oligo microarrays", Nucleic Acids Res. May 24, 2005;33(9):e84.

Steric factors influencing hybridization of nucleic acids to oligonucleitde arrays, 1997, Nucleic Acids Research, 25, 1155-1161.

Hui et al, Stratagies for cloning unknown cellular flanking DNA sequences from foreign integrants, 1998, CMLS, Cell. Mol. Life Sci., 54, 1403-1411.

New England Bio Labs, Enzyme finder by sequence.

Kohda et al, A simple and efficient method to determine the terminal sequences of restriction fragments containing known sequences, 200, DNA Research, 7, 151-155.

FIG. 7
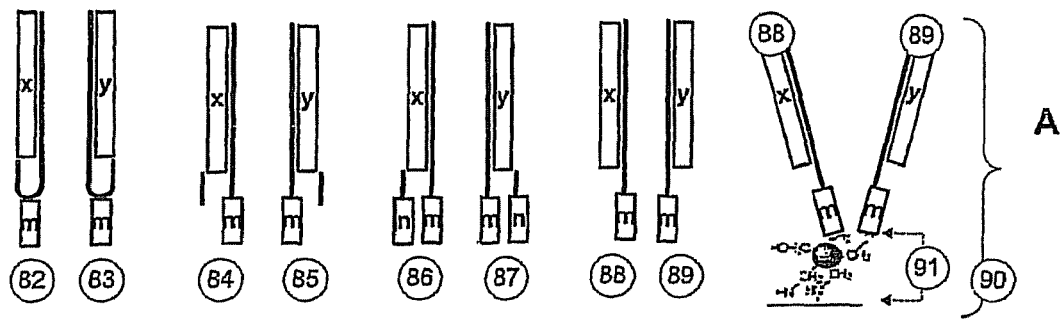
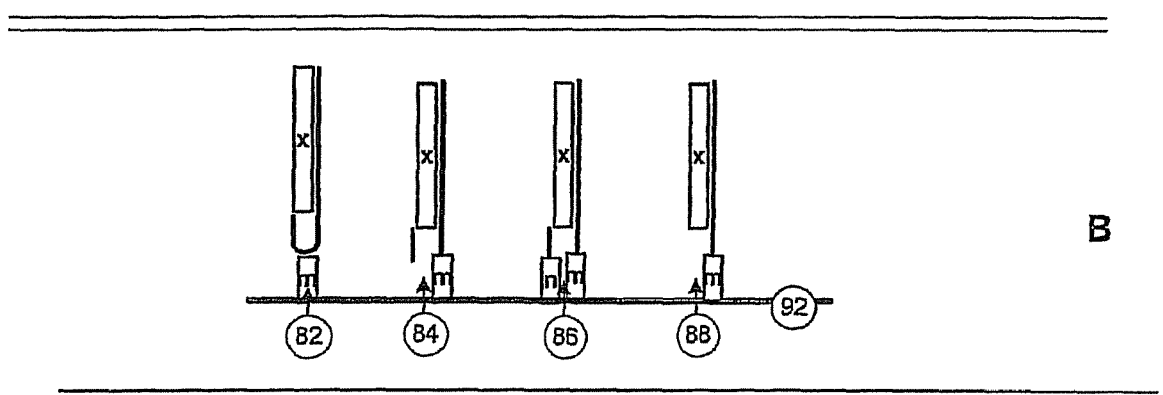
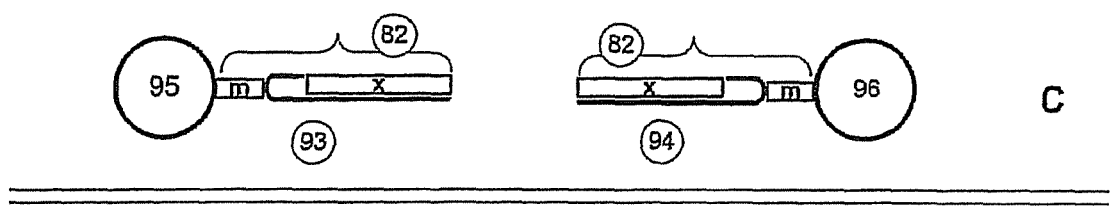
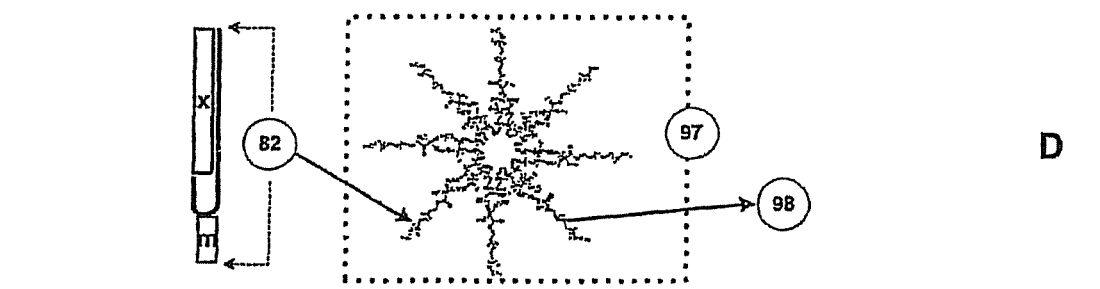

FIG. 8
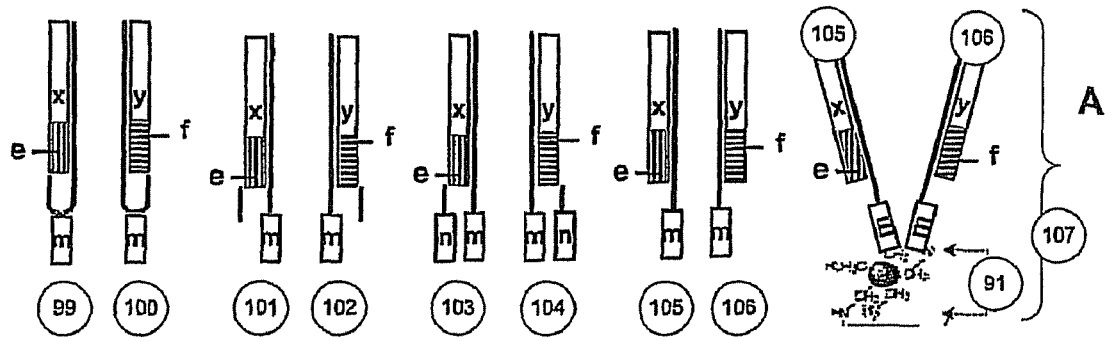
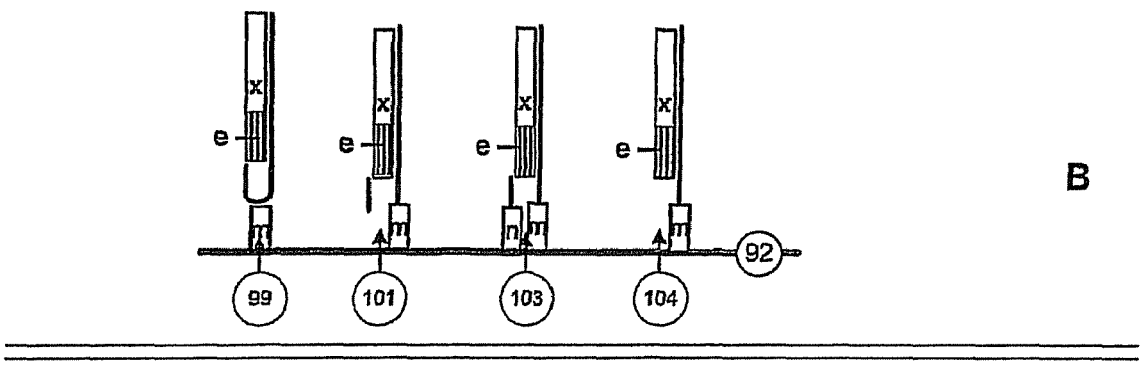
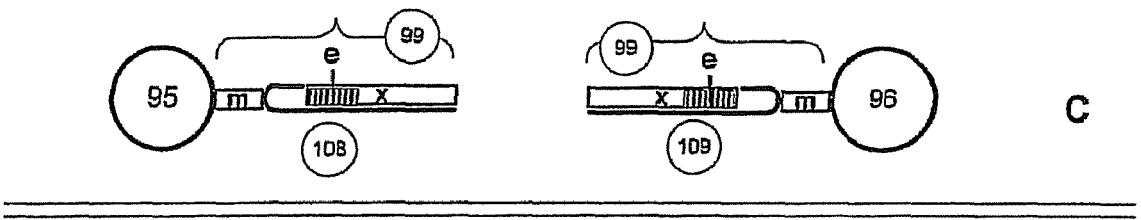
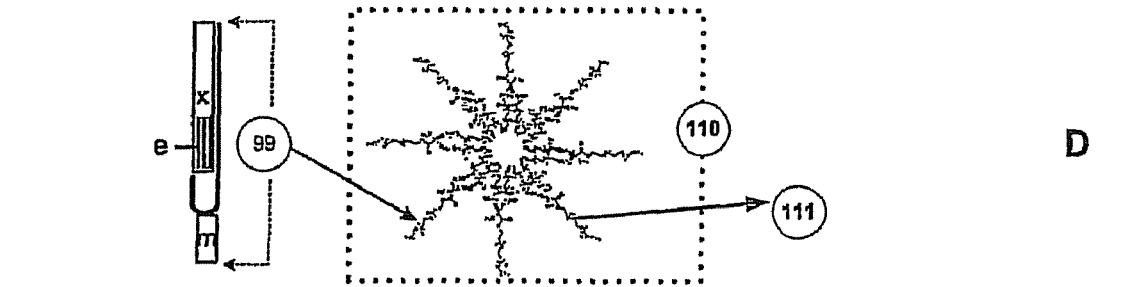

FIG. 11
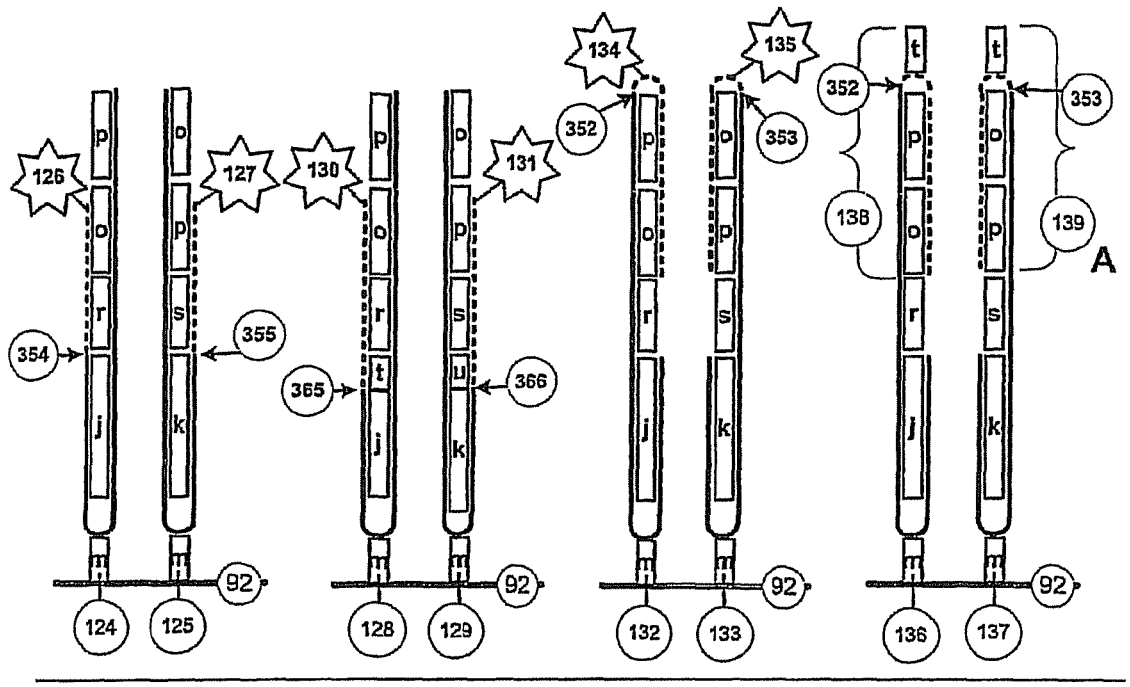
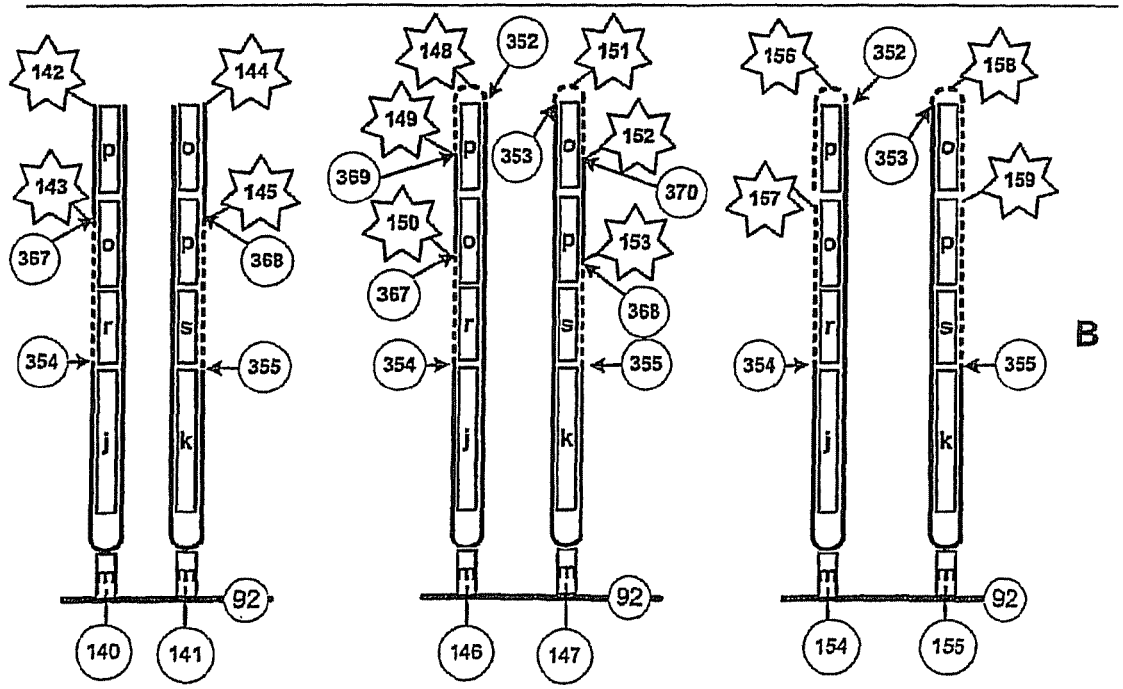

FIG. 12
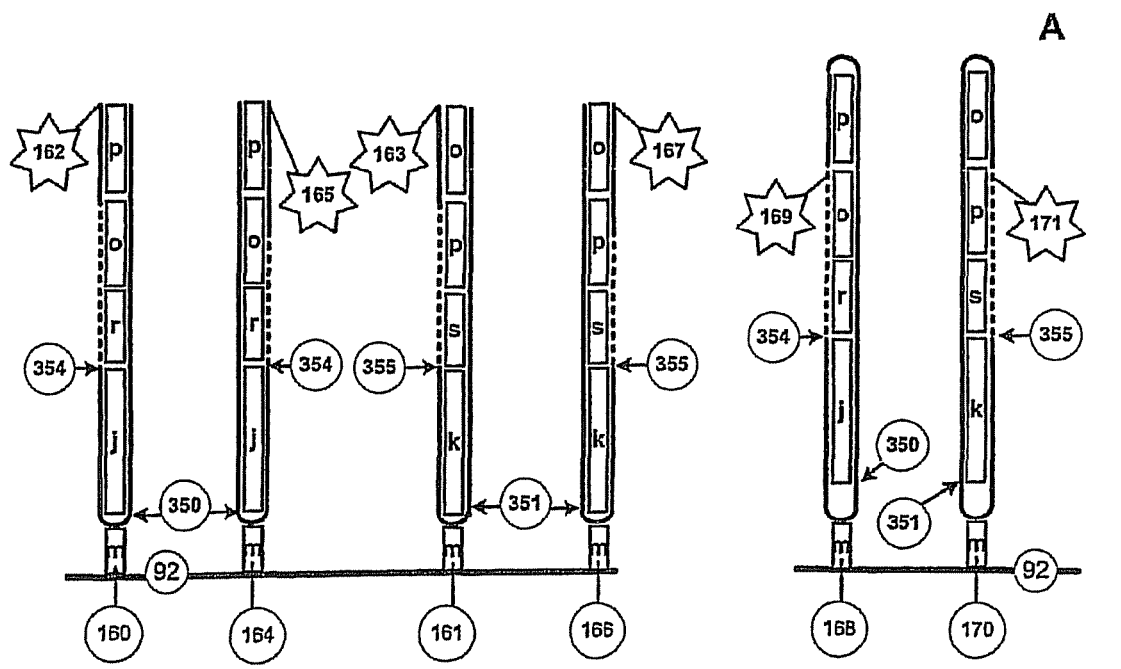
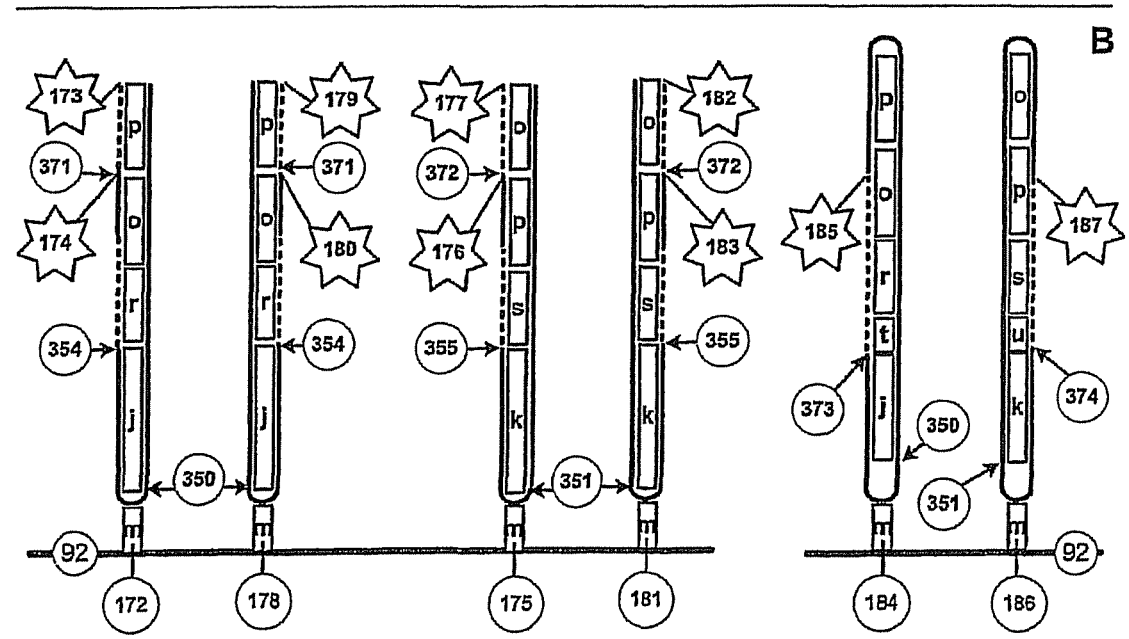

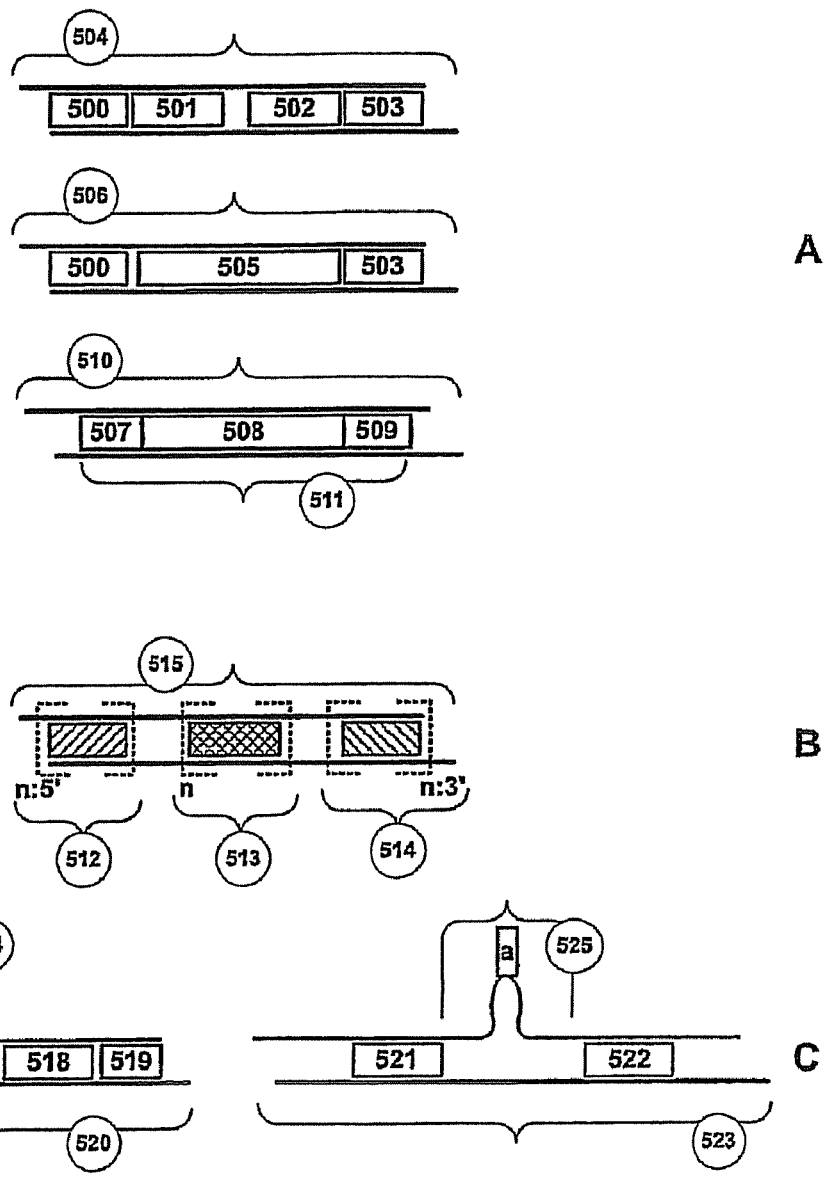

PRODUCING, CATALOGING AND CLASSIFYING SEQUENCE TAGS

CROSS REFERENCE TO RELATED APPLICATIONS

This application claims priority to U.S. Nonprovisional application Ser. No. 11/143,209, dated Jun. 2, 2005 which claims priority to U.S. Provisional Application Ser. No. 60/576,379 filed Jun. 2, 2004, all of which are incorporated herein by reference in their entirety.

BACKGROUND

This disclosure is generally in the field of nucleic acid characterization and analysis, and specifically in the area of analysis and comparison of genes, gene expression patterns, nucleic acid samples, genomes, and genetic biomarkers.

The analysis of gene-expression and genome patterns is one of the most promising approaches for studying cellular molecular circuitry, biological diversity, and developmental biology. These studies may elucidate the identity and role of molecular targets, which will subsequently play an important role in developing efficacious human and veterinary therapeutics; novel technologies for biodefense; biological agents for bioremediation; and agricultural advances including predator resistant strains, superior crop yields, and increased shelf life. Furthermore, routine medical diagnostics will add genetic profiling assays for drug administration and patient therapeutic monitoring.

Differential Display and DNA Microarray gene expression profiling techniques have emerged as the predominate methods for whole genome gene expression analysis. These technologies measure changes in gene expression among cellular states to determine life processes. Exemplary conditions that effect cellular states include temporal, spatial, and experimental treatments, or any combination thereof. Types of state changes observed include genome-wide effects of known regulators or transcription factors, the biological components of the cellular machinery that generate the genomic signals, and measurements of over- or under-active regulators or transcription factors, for example. In addition, these technologies may be employed in the study of comparative genomics and the discovery of genetic biomarkers.

Classical approaches to gene-expression analysis, such as northern blotting or plaque hybridization, are time-consuming and material-intensive methods to analyze mRNA-expression patterns. Additionally, these early methods encountered problems with cDNA-probe complexity for differential hybridization. Subtractive hybridization was developed to address this problem using a method to enrich for cDNA targets that represent mRNAs that are uniquely expressed in one cell but not in another. This method reduced the complexity, leaving behind only single-stranded cDNAs that represented a few differentially expressed genes.

The Differential Display (DD) method overcame the limitation of these earlier methods that could be error-prone, insensitive, non-systematic, and laborious. Furthermore, DD is an "open system" not requiring any knowledge of RNA or gene sequences. DD simplified the experimental process with a one-tube method and increased the speed in the identification of expressed genes. DD systematically produces sets of nucleic acid fragments by amplifying anchored mRNA with a primer of arbitrary sequence. The fragments from each primer are displayed side-by-side using denaturing polyacrylamide gel electrophoresis. Comparison of DNA fragment patterns between or among relevant RNA samples indicate differences in gene expression.

Variations in the original DD protocol used strategies employing variations of enzyme sets, primers sets and combinations thereof. These derivate methods of DD included RFLP-Based DD strategies, Targeted DD, Integration of Subtractive Hybridization, and Integration of DD with DNA Microarrays.

SAGE (Serial Analysis of Gene Expression) is an open system sequence-based approach to identify differentially expressed genes. In this method, short (10-14 base pair) nucleic acid tags are generated by restriction digestion, amplified by PCR and ligated, producing concatemers, which are further analyzed by electrophoretic sequencing methods. The tag identities are sufficient in unequivocally corresponding to genes. Furthermore, the frequency of the tags is a measure of their expression level. A limitation of SAGE is that the corresponding gene can be identified only for the tags deposited in public repositories, imposing a dependency on available databases. Variants have been published that circumvent some limitations of SAGE.

High-density DNA microarrays advanced gene expression profiling technology, enabling simultaneous analysis from tens of thousands of genes on a standard laboratory microscope slide. cDNA or oligonucleotide capture probes of known sequence are systematically deposited at known locations on a solid support, i.e., "chips". The capture probe positions are commonly referred to as addresses. Fluorescence labeled mRNA or cDNA targets are hybridized to complementary capture probes, signal detected by multi-color microarray laser scanner and displayed with image analysis software. Predominantly, DNA microarrays are closed systems, requiring the knowledge of RNA or gene sequences.

Other innovative open systems for gene-expression profiling, producing sequence tags from RNA or cDNA using various adapter driven methods, have been described. These methods use a variety of strategies whereby a cDNA sample is systematically digested into fragment pools; a fragment is ligated to one or more adapters, and amplified. Subsequent steps include sorting the tags by means of adapter mediated indexing. All these methods are significant improvements over DD by explicitly providing tag sequence information.

BRIEF SUMMARY

This invention overcomes limitations in gene-profiling open systems by systematically producing sequence tags from a chimeric nucleic acid having a customized nucleic acid bridge, wherein the bridge is disposed between two cDNA fragments. In addition, this method can achieve massive simultaneous detection of sequence tags without requiring pooling, sorting, or adapter mediated indexing. Furthermore, the method disclosed has an open architecture designed to include a chemically closed system, allowing systematic control in managing target complexity, sequence tag complexity, detection specificity, greater number of independent target measurements and broader scope in signal multiplexing not available with methods known in the art for nucleic acid detection and analysis.

A method for cataloging and classifying sequence tags produced from linear chimeric nucleic acid intermediates comprising target nucleotide sequences and a duplex nucleic acid bridge is described. The method includes a sequence tag producing phase, an optional capture phase, an optional labeling phase, an optional detection phase, an optional sequence tag identity processing phase, an optional cataloging phase, an optional catalog indexing phase, an optional classification phase, and combinations comprising one or more of the foregoing phases.

In an exemplary embodiment, the sequence tag producing phase includes generating a population of target nucleic acid fragments by, for example, digesting a nucleic acid sample; covalently coupling duplex nucleic acid bridges having compatible ends to the target nucleic acid fragments to form linear chimeric nucleic acid intermediates; shortening the linear chimeric nucleic acid intermediates with cleaving agents having a recognition sequence in the bridge but that cleave outside the bridge; adding universal primers and producing a population of sequence tags by amplification. A quality control aspect of the method allows for production of subpopulations of sequence tags having the same length. Furthermore, managing sequence tag complexity may also be achieved by, for example, controlling sequence tag diversity and amounts in the nucleic acid sample digestion step, the amplification step, or both.

In an exemplary embodiment, the next phase of the process includes the capture phase. This phase includes, for example, providing a support with capture probes. The capture probes may be immobilized on a substrate producing an addressable array, or immobilized on addressable beads, or bound to addressable populations of polymeric micelles. In an embodiment using beads, the bead identities may be distinguished by a physical property such as size, dimension, label, or any combination thereof. In another embodiment using polymeric micelles, the polymeric micelle identities may be distinguished by a reporter agent bound to the polymeric micelle hydrophobic core. The capture probes, optionally with a partial duplex addressable portion, can be contacted with a population of sequence tags under conditions effective to hybridize and optionally covalently couple the addressable array-specific portions of the sequence tags to the capture probes in a base-specific manner. Prior to hybridization, the sequence tags can be prepared as single-stranded or partial duplex sequence tags. Partial duplex sequence tags may have two covalent coupling sites with the capture probe. In some embodiments, a hairpin partial duplex sequence tag may be employed, where an end of the single stranded sequence tag is a portion of the bridge that is capable of forming a hairpin.

In an exemplary embodiment, the labeling phase includes labeled oligonucleotide detector probes that can be hybridized and optionally covalently coupled to a single stranded portion of the sequence tags, wherein the portion is not part of the addressable array-specific portion, i.e., the portion that hybridizes to the capture probes. In some embodiments, single-stranded sequence tags are contacted with labeled detector probes after the capture phase. Partial duplex sequence tags can be produced by hybridizing and optionally covalently coupling a detector probe prior to the capture probe phase.

In another exemplary embodiment, the detection phase is the process of surveying labeled capture probe-sequence tag hybrids. An addressable support can be analyzed to identify addresses having labels. Furthermore, subsequent iterations of labeling and detection are allowed by related methods. Releasing and detecting labels from capture probe-sequence tag hybrids is a method for indirectly surveying the identity of addresses having labeled captured probe-sequence tag hybrids. Further aspects of detection include processing the detected signal, and determining and recording the amount of label at each address. In an embodiment using polymeric micelles as the addressable support, labeled capture probe-sequence tag hybrids can be sorted, prior to analysis by size, reporter agent, capture probe-sequence tag hybrid composition, or any combination thereof.

After the detection phase, sequence-specific signatures for each detected address can be determined in the sequence tag identity processing phase. Sequence-specific data can be collated and analyzed from the sequence tag producing phase; the capture phase, the labeling phase; and/or the detection phase in determining the sequence tags' identities, wherein a sequence tag identity is comprised of a sequence-specific signature.

The cataloging phase is a process to systematically store the sequence tag and its' sequence-specific signature in a database. Methods suitable for cataloging are well known to those skilled in the software database art and require no further description. Information and process parameters suitable to produce, capture, label, and detect can be systematically stored in an electronic database and associated to the cataloged sequence tags. Furthermore, a nucleic acid sample processing history used in producing sequence tags can be reconstituted from a catalog.

The catalog indexing phase is a process to systematically group and/or order a catalog into indexing elements. Indices are calculated using values from of certain fields in a catalog. Methods suitable for catalog indices are well known in the art.

The analysis of a catalog and/or a catalog index may include classification encoding into a biological context, a semantic entity context, or both; and storage in a classifier database. Furthermore, the method allows for a direct association between a sequence tag and its classifiers. There are a variety of resources for selecting classifiers. Examples of resources are public and proprietary ontologies, taxonomies, nomenclatures, or any combination thereof. Examples of classifiers are biological entities such as organism, strain, gene, gene family, ortholog, paralog, homolog, regulatory element, exon, introns, and any combinations thereof. Other examples of classifiers are semantic entities computed from literature such as events, locations, people, and chemicals, and any combination thereof (U.S. Patent Applications 20050075859 and 20040243645) or the relationships between semantic entities. A catalog analysis can produce a sequence tag signature classifier. For example, a signature classifier may be a difference signature resulting from comparing a reference and tester nucleic acid sample. A catalog index element can be a classifier. For example, a suitable catalog index element may be comprised of the processing parameter's probe constant sequence (PCS), first cleaving agent, and capture probe. The number and types of classifiers is unbounded and grows with increasing diversity in a sequence tag catalog.

The presence, identity, or cellular state of specific organisms can be detected by analyzing the resulting classifier database. Changes and differences in gene expression patterns can also be detected by comparing sequence tag signatures of RNA and/or mRNA from different cell samples. Furthermore, changes and differences in genomic patterns can also be detected by comparing sequence tag signatures of genomes from different cell samples. Sequences stored in a catalog and a catalog index can also be used to produce a set of probes or primers that is specific for the source of a nucleic acid sample.

BRIEF DESCRIPTION OF THE SEVERAL
VIEWS OF THE DRAWINGS

FIGS. 1 to 4 illustrate method of producing nucleic acid sequence tags.

FIG. 1 is a schematic representation of an embodiment of the invention for producing sequence tags employing a first bridge (C5). A1 and A2 shows double stranded DNA (dsDNA). The first cleaving agent produces a population of target fragments. B3 and B4 are digested products of A by a first cleaving agent, also called first and second target nucleic acids. C5 is a first bridge, comprising two Type IIS recognition sites (portions r and s) and two primer sites (portions o and p). D shows a chimeric nucleic acid intermediate indicated by D6. The chimeric nucleic acid intermediate is produced by ligating a first target (3) and a second target (4) to a first bridge (5), wherein a first bridge is flanked by a first target and a second target. E shows first bridges comprising terminal ends ligated to biotinylated partial duplexes, also referred as a blocker agent (Hairpin partial duplex or partial duplex) to deactivate excess bridge. The biotin attachment moiety is indicated by (a). An embodiment described is a step to add a reagent to deactivate the excess bridge. Preferably, under suitable conditions, the duplex bridge is denatured and contacted with the reagent. E11 and E12 are first bridges ligated to partial duplexes (E7 and E8). E13 and E14 are first bridges ligated to biotinylated hairpin partial duplexes (E9 and E10). F illustrates second cleaving agent (F15 and F16). Cleaving occurs at one site away from bridge from each agent. The first bridge has two recognition sites which are indicated by portions (r) and (s). G shows a cleaved product of F, a shortened chimeric nucleic acid intermediate (F27), comprising a first bridge flanked by target portions (t and u). H shows amplified products indicated by H18 and H21, wherein the primers portions are indicated by numbers 360 and 361. Amplification methods used are known in the art such PCR, RCA, SDA and HCR for example. Not shown, but described, are adding amplification primers with an attachment moiety. Preferably, a primer's 5'-end base is biotinylated. H17 and H20 are the strands of the shortened chimeric nucleic acid intermediate (27). Various priming methods are known in the art. Primers are selected to produce desired sequence tags. Optionally, one or more primers can be employed. Available strategies are determined by the bridge design. Amplification strategy determines type of target fragment populations. I shows the post amplification products. Double stranded (ds) sequence tags are indicated by I23 (first ds sequence tag) and I24 (second ds sequence tag). Single stranded (ss) sequence tags are indicated by I25 (first ss sequence tag) and I26 (second ss sequence tag). The target portion of the sequence tags are indicted by portions (t) and (u).

Figure 2:
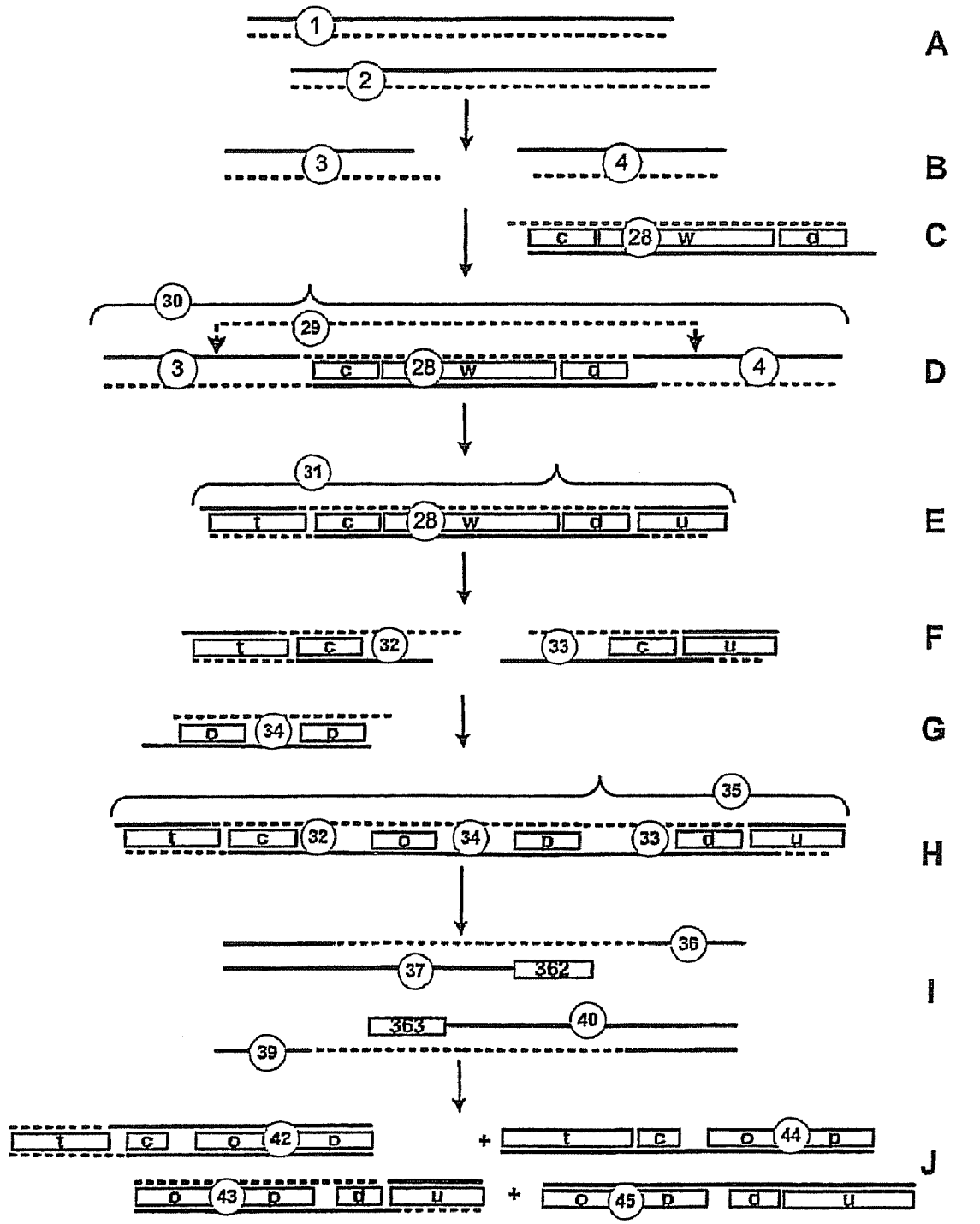

FIG. 2 is a schematic representation of an embodiment of the invention for producing sequence tags employing a first bridge and a second bridge. The first cleaving agent produces a population of target fragments. A1 and A2 shows double stranded DNA DNA (dsDNA). B3 and B4 are digested products of A by a first cleaving agent, also called first and second target nucleic acids. C shows a cleavable bridge (first bridge) with an embedded restriction recognition site which cleaves outside both ends of the bridge. C28 is a first bridge, wherein portion (c), (w), and (d) are portions of the Type III recognition site. Portion (w) is a Type II recognition site. D shows a linear chimeric nucleic acid intermediate indicated by D30. The linear chimeric nucleic acid intermediate is produced by ligating a first target (3) and a second target (4) to a first bridge (28), wherein a first bridge is flanked by a first target and a second target. Also illustrated in D is the second cleaving agent indicated by D29. This cleaving agent can be a suitable Type III or Type II subtype (i.e.: Type IIB). E shows a shortened chimeric nucleic acid intermediate, a product produced by digesting the linear chimeric nucleic acid intermediate (30) with a cleaving agent (29). A shortened chimeric nucleic acid intermediate is indicated by E31, comprising a first bridge portion (28) flanked by target portions (t and u). F shows digested products of E by a third cleaving agent, wherein the third cleaving agent is different from the first cleaving agent. Cleaving occurs within the first bridge. G34 is a second bridge comprising two primer sites (portions o and p). H shows a modified shortened chimeric nucleic acid intermediate, a product produced by ligating the digested products, indicated by numbers 32 and 33, to a second bridge (34). A modified shortened chimeric nucleic acid is indicated by H35, comprising a second bridge (34) flanked by digest products (32 and 33). I shows amplified products indicated by I37 and I40, wherein the primers portions are indicated by numbers 362 and 363. Amplification methods used are known in the art such PCR, RCA, SDA and HCR for example. Not shown, but described, are adding amplification primers with an attachment moiety. Preferably, a primer's 5'-end base is biotinylated. I36 and I37 are the strands of the modified shortened chimeric nucleic acid intermediate (35). Various priming methods are known in the art. Primers are selected to produce desired sequence tags. Optionally, one or more primers can be employed. Available strategies are determined by the bridge design. Amplification strategy determines type of target fragment populations. J shows the post amplification products. Double stranded (ds) sequence tags are indicated by J42 (first ds sequence tag) and J43 (second ds sequence tag). Single stranded (ss) sequence tags are indicated by J44 (first ss sequence tag) and J45 (second ss sequence tag). The target portion of the sequence tags are indicted by portions (t) and (u).

Figure 3:
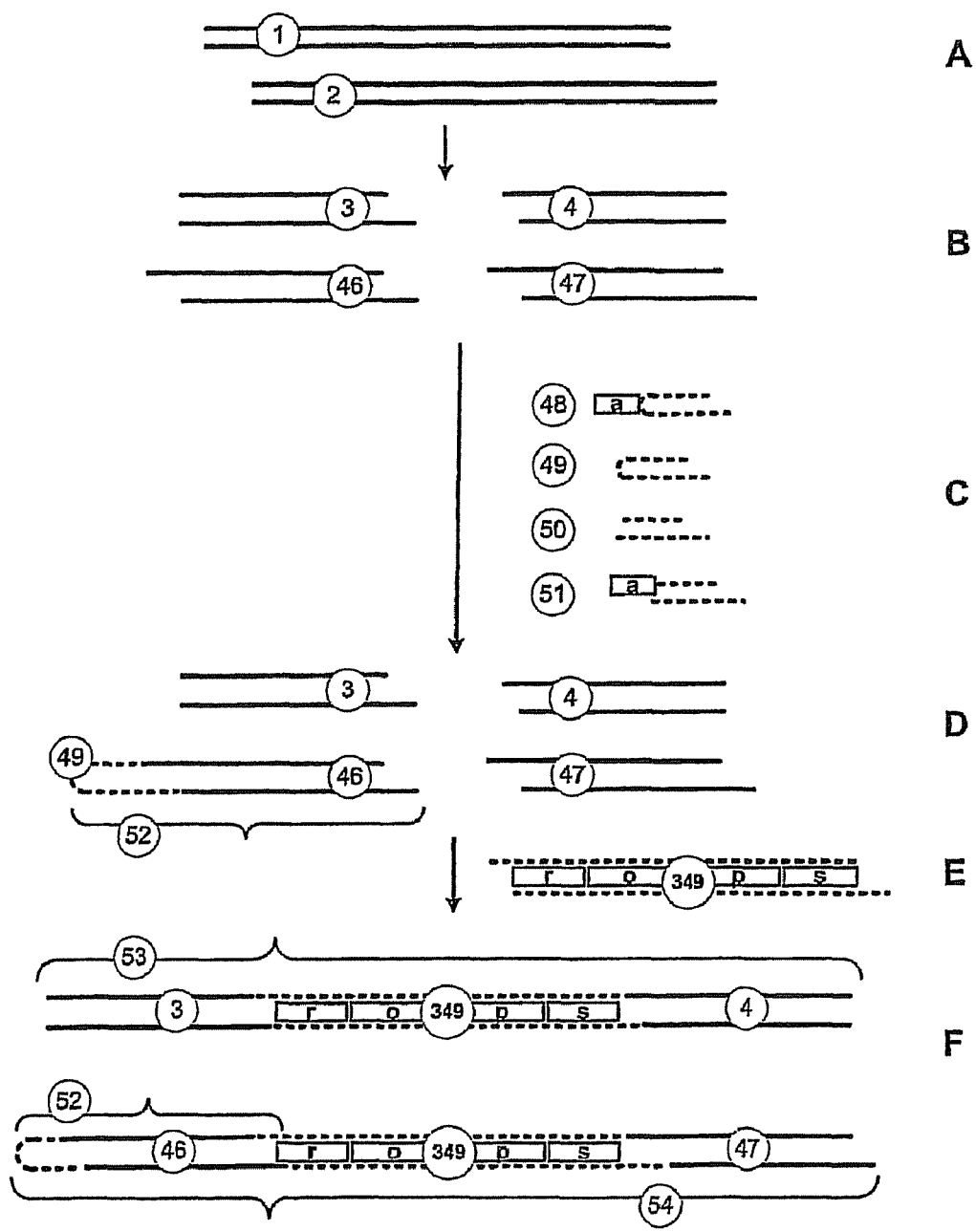

FIG. 3 is a schematic representation an embodiment of the invention for producing linear chimeric nucleic acid intermediates comprised of deactivated terminal ends. The first cleaving agent produces a population of target fragments. A shows double stranded DNA (dsDNA) indicated by A1 and A2. B shows products produced by a first cleaving agent cleaving dsDNA, wherein the cleaving agent's recognition sequence comprises one or more ambiguous bases. Digested products produced by cleaving dsDNA (A1 and A2) are indicated by B3, B4, B46 and B47. B3 is a target nucleic acid fragment having one sticky end (5' overhang of dsDNA). B4 is a target nucleic acid fragment having one sticky end (3' overhang of dsDNA). B46 is a target nucleic acid fragment having two sticky ends, wherein the sticky ends have different sequence. B47 is a target nucleic acid fragment having two sticky ends which have the same sequence. C shows examples of partial duplexes, also called deactivation reagents. An embodiment described, is to hybridize and couple a partial duplex, wherein one end is non-reactive and the other end has a sticky end compatible with a subpopulation of fragments. C48 is a hairpin partial duplex comprising an attachment moiety (i.e. biotin) at the hairpin terminal end. The attachment moiety is indicated by (a). C49 is a hairpin partial duplex with a non-reactive hairpin terminal end. C50 is a partial duplex with a non-reactive terminal end. C51 is a partial duplex comprising an attachment moiety (i.e. biotin) at a terminal end. D shows an embodiment where a target nucleic acid fragment, in a set of fragments comprising a plurality of stick ends, is ligated to a partial duplex. D52 is produced by hybridizing and ligating a hairpin partial duplex (C49) to a target nucleic acid fragment (B46). E shows a first bridge comprising primer sites and restriction enzyme recognition sites. A first bridge is indicated by E349, wherein the primer sites are indicated by portions (r) and the restriction enzyme recognition sites are indicated by portions (o) and (p). F shows chimeric nucleic acid intermediates indicated by F53 and F54. F53 is produced by ligating target fragments indicated by numbers 3 and 4 with the first bridge (349). A chimeric nucleic acid intermediates comprising a deactivated terminal end indicated by F54, is produced by ligating target fragments indicated by numbers 52 and 47 with the first bridge (349).

Figure 4:
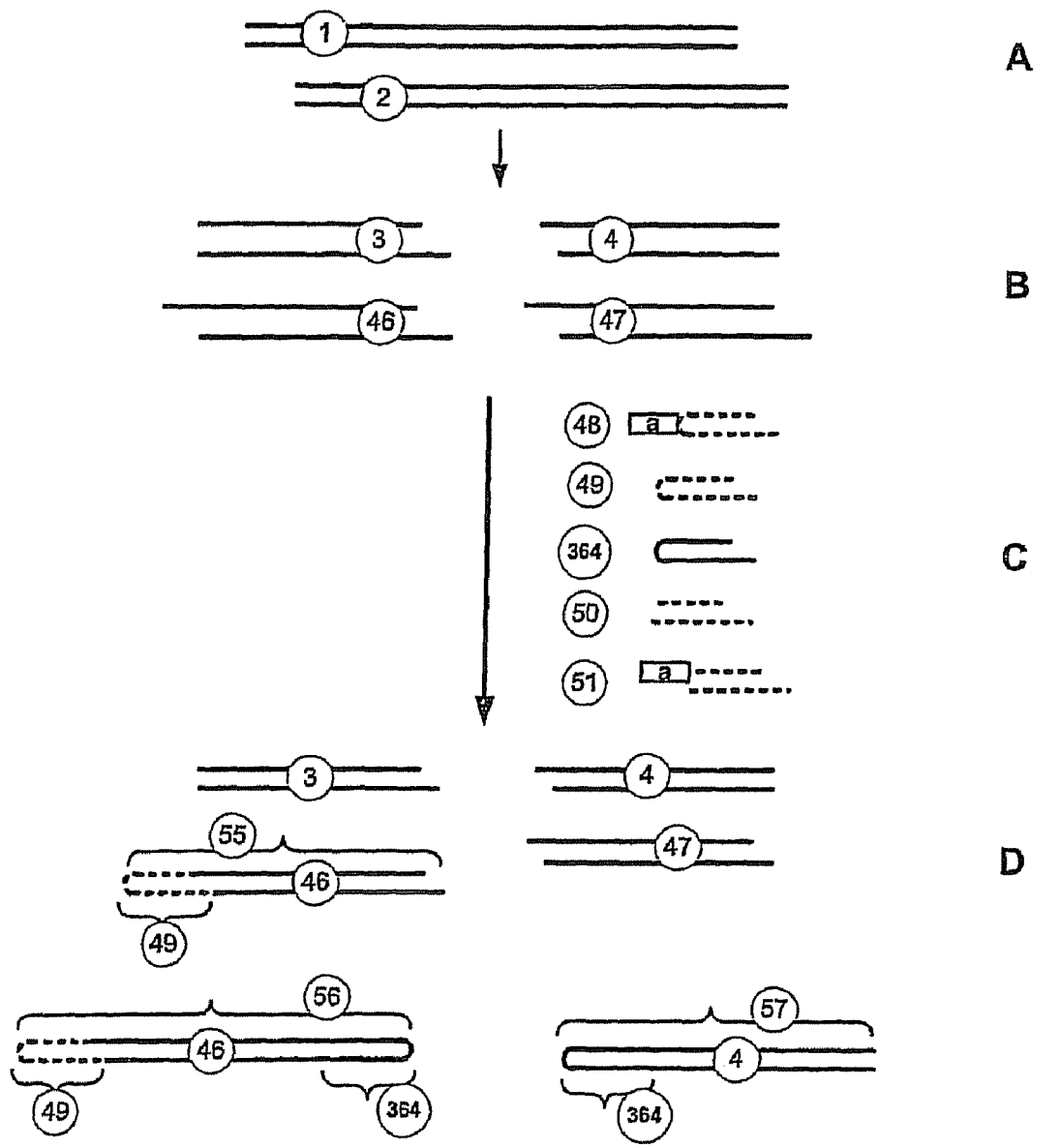

FIG. 4 is a schematic representation of an embodiment of the invention for producing target nucleic acid fragments comprised of one or more deactivated terminal ends. A1 and A2 shows dsDNA. B3, B4, B46 and B47 are the digested products of A by a first cleaving agent having a cut site offset from its recognition sequence. B3 shows a target nucleic acid fragment having one sticky end (5' overhand of dsDNA). B4 shows a target nucleic acid fragment having one sticky end (3' overhang of dsDNA). B46 shows a target nucleic acid fragment having two sticky ends, wherein the sticky ends have different sequence. B47 shows a target nucleic acid fragment having two sticky ends which have the same sequence. C shows examples of partial duplexes, also called deactivation reagents. C48 is a hairpin partial duplex comprising an attachment moiety (i.e. biotin) at the hairpin terminal end. C49 and C364 are hairpin partial duplexes with a non-reactive terminal end. C50 is a double stranded partial duplex. C51 is a double stranded partial duplex comprising an attachment moiety (i.e. biotin) at a terminal end. The attachment moiety is indicated by portion a. D shows ligation of the target fragments and the partial duplexes. D55 and D57 are target nucleic acid fragments coupled to a target hairpin partial duplex. D56 is a target nucleic acid fragment coupled to two hairpin partial duplexes.

Figure 5:
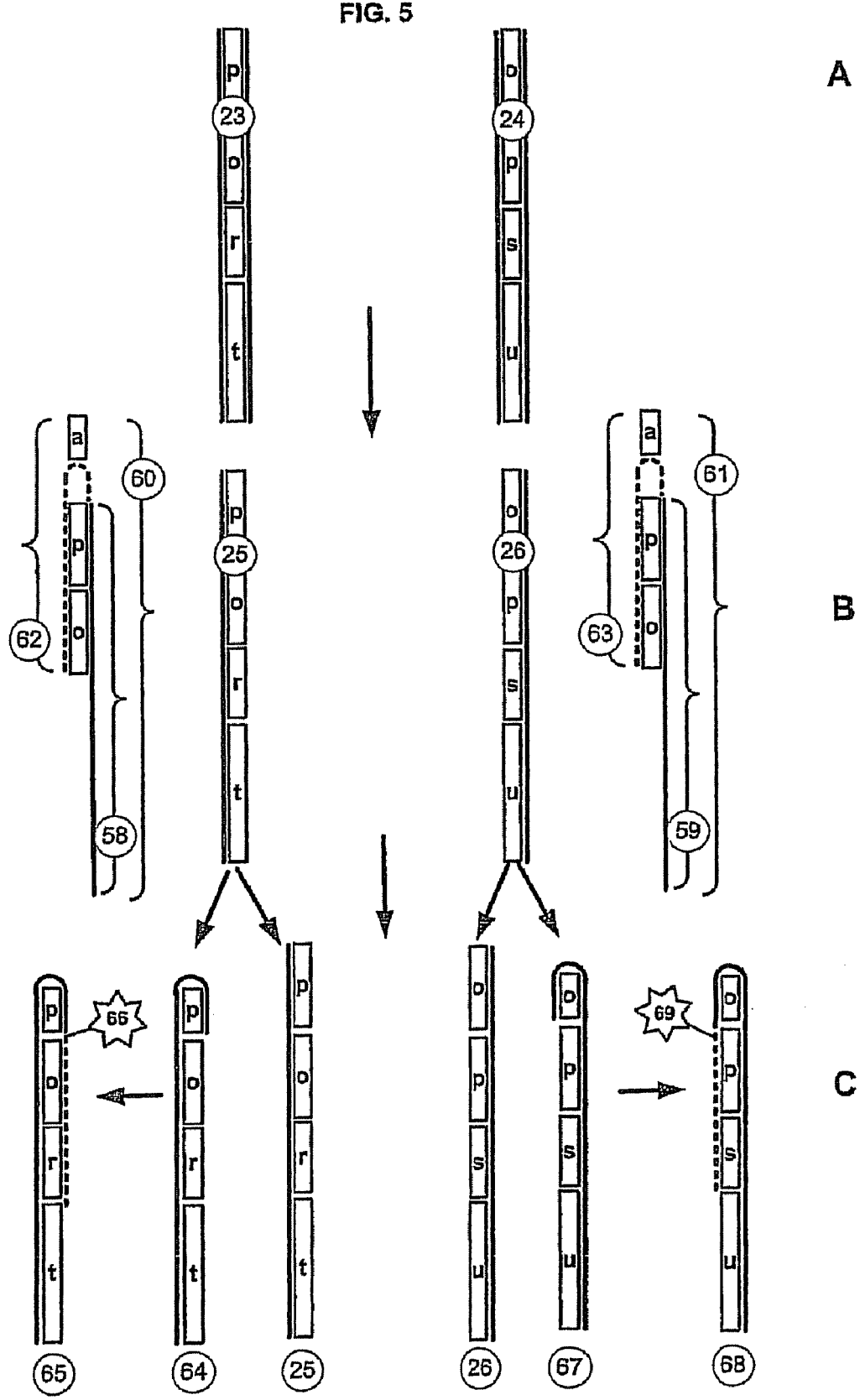

FIG. 5 illustrates the preparation of single-stranded sequence tags for an optional capture phase.

FIG. 5 is a schematic representation of an embodiment of the invention for the preparation of double stranded sequence tags for an optional capture phase. A shows double stranded (ds) sequence tags comprising indicated by A23 and A24, wherein a sequence tag comprises a cleavable recognition sequence (recognition sequence for a second cleaving agent), a primer binding site, and a target nucleic acid portion, wherein a target nucleic acid portion has an address, wherein an address is an array-specific address portion. Cleavable recognition sequences are indicated by (r) and (s), primer binding site are indicated by (o) and (p), and target nucleic acid portions are indicated by (t) and (u). The address portion (t and u) shown here are adjacent to the Type IIS recognition site (r and s). Another embodiment of the invention has the address portion down stream of the Type IIS recognition site. B shows products from denaturing double stranded sequence tags into single stranded sequence tags and contacted with reducing reagents. B62 and B63 are hairpin partial duplex reducing reagents comprising a biotin attachment moiety, also called deactivation reagents. The attachment moiety is indicated by (a). B60 and B61 are products from ss sequence tags (B58 and B59) coupled with biotinylated hairpin adapters (B62 and B63). An embodiment prevents B60 and B61, preferably by removal, from participating in the capture phase, employing a solid phase capture method known in the art. C shows prepared ss sequence tags. C25 and C26 are unmodified ss sequence tags. C64 and C67 are hairpin ss sequence tags, wherein the primer portions of the bridge (p and o) form a terminal hairpin. C65 and C68 are labeled sequence tags, produced by hybridizing and ligating the labeled detector probes (66 and 69). Hairpin sequence tags are designed to be used with capture probes that are attached to substrates whose address has a direct readout. Commercial examples having suitable attachment substrates and readout include CyVera barcode beads, Luminex dye beads, Illumina's fiber optic bundles, and GeneXP's BioGridArray.

Figure 6:
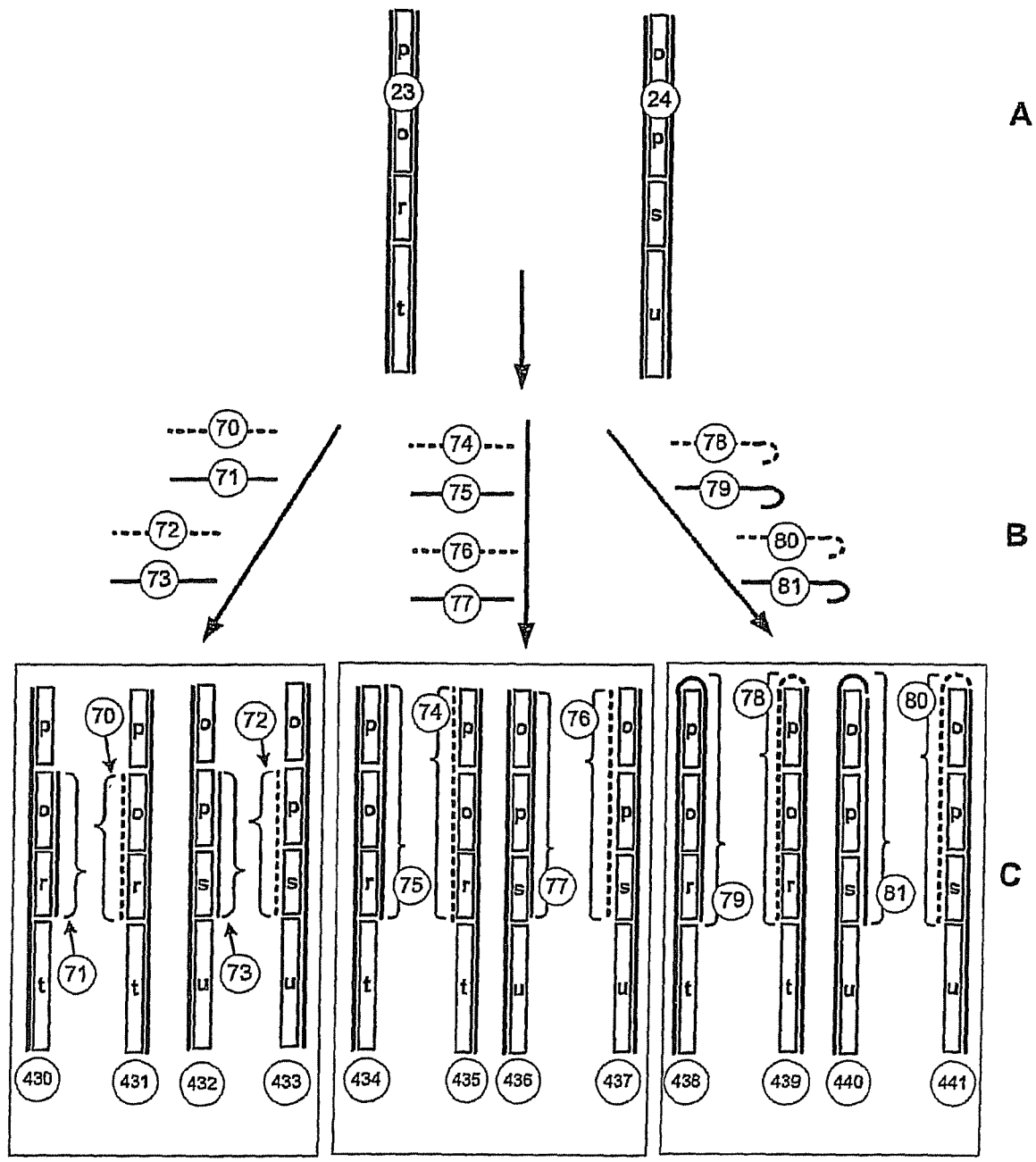

FIG. 6 illustrates the production of partial hybrid sequence tags.

FIG. 6 is a schematic representation of another embodiment of the invention for the preparation of double stranded sequence tags for an optional capture phase. A shows double stranded (ds) sequence tags comprising indicated by A23 and A24, wherein a sequence tag comprises a cleavable recognition sequence (recognition sequence for a second cleaving agent), a primer binding site, and a target nucleic acid portion, wherein a target nucleic acid portion has an address, wherein an address is an array-specific address portion. Cleavable recognition sequences are indicated by (r) and (s), primer binding site are indicated by (o) and (p), and target nucleic acid portions are indicated by (t) and (u). B shows ligator probes, comprising complementary sequence to portions of single stranded (ss) sequence tags. Ligator probes comprise either nucleic acids or peptide nucleic acids (PNA). Ligator probes serve two functions after being contacted with ss sequence tags. First, they prevent ss sequence strands from reannealing. Second, they provide two points of ligation, enhancing specificity via favorable thermodynamic base-stacking in the optional capture phase. Another embodiment of the invention employs labeled ligator oligonucleotide probes, also called labeled detector probes. Ligator oligonucleotides probes are indicated by B70, B71, B72, B73, B74, B75, B76, and B77. Hairpin ligator probes are indicated by B78, B79, B80 and B81. C shows thermal stable partial duplex sequence tags. These tags are produced by denaturing ds sequence tags and contacting with ligator probes with ss sequence tags. C430, C431, C432, and C433 are products having the ligator probe hybridized to the ss sequence tag, wherein the ligator probe's terminal end is abutting the ss sequence tag portions (t) and (u). C434, 435, 436 and C437 are products having the ligator oligonucleotide hybridized to the ss sequence tag, wherein a terminal end is complementary to a terminal end of the ss sequence tag and a terminal end is abutting the sequence tag portion (t) and (u). C438, C439, C440 and C441 are products having a hairpin ligator probe hybridized and ligated to the ss sequence tag, wherein a terminal end is complementary to a terminal end of the ss sequence tag and a terminal end is abutting the ss sequence tag portion (t) and (u).

FIGS. 7 and 8 illustrate the coupling of capture probes to the sequence tags to form sequence tag-capture probe hybrids.

FIG. 7 is a schematic representation of an embodiment of the invention's capture phase to produce sequence tag-capture probe hybrids. A shows capture probe types comprising partial duplexes and oligonucleotides, wherein a capture probe has a variable address portion, (also called the variable sequence portion) and an activated linker. Capture probes are covalently attached to an immobilized substrate through the activated linker. PNA capture probes are the same as number of types of nucleic acid capture probes, wherein PNA capture probe's composition comprises a peptide backbone. The variable address portions are indicated by (x) and (y). Capture probe attachment linkers are indicated by portions (m) and (n). A82 and A83 are hairpin partial duplex capture probes comprising an attachment linker. A84 and A85 are bi-molecular partial duplex capture probes comprising an attachment linker, wherein the attachment linker is on the strand comprising the variable address portion. A84 and A85 are bi-molecular partial duplex capture probes comprising two attachment linkers (m and n). A88 and A89 are oligonucleotide capture probes with attachment linkers. A90 is a dendrimeric capture probe comprising oligonucleotide capture probes (88 and 89). A91 is an immobilized dendrimer particle. B shows an array of capture probes immobilized on a solid substrate (B92)—a hairpin capture probe (B82), two bi-molecular partial duplex capture probes (B84 and B86) and an oligonucleotide capture probe (B88). C shows examples of capture probes immobilized to beads. Described is the use of microbeads (a.k.a. micro-partials) as an immobilized substrate for capture probes, wherein a microbead has unique distinguishable characteristics, are pooled into sets or array of sets. C93 is a capture probe immobilized on a microbead with an embedded barcode (U.S. Patent Application 20040075907), wherein the hairpin capture probe (C82) is linked to an encoded bead (C95). C94 is a capture probe immobilized on a microbead with incorporated fluorochromes (U.S. Pat. No. 5,981,180), wherein a hairpin capture probe (C82) is linked to a dye colored bead (C96). D is an embodiment of a polymeric micelle that encapsulates hydrophobic molecules, such as fluorescent dyes and Quantum Dots, for example. These polymers are designed with a branched, hydrophobic interior (core) and hydrophilic exterior (shell) to maintain physical properties characteristic of conventional micelles, but with enhanced thermodynamic stability. Capture probes are covalently linked to hydrophilic appendages (also called hydrophilic branches) specific for targeting moieties, wherein the polymeric micelle may be covalently attached to an immobilized substrate via its hydrophilic appendages specific for attachment moieties. D97 is a polymeric micelle comprising hairpin capture probes (D82) linked to the polymeric micelle's hydrophilic branches (D98).

FIG. 8 is a schematic representation of another embodiment of the invention's capture phase to produce sequence tag-capture probe hybrids. A shows capture probe types, comprising partial duplex and oligonucleotide, wherein a capture probe has a variable address portion, a constant address portion and an activated linker, wherein the constant address portion is flanked by the variable address portion and the duplex portion. Capture probes are covalently attached to an immobilized substrate through the activated linker. PNA capture probes are the same as number of types of nucleic acid capture probes, wherein PNA capture probe's composition comprises a peptide backbone. Variable address portions, also called variable sequence portion, are indicated by (x) and (y). Constant address portions, also called constant sequence portion, are indicated by (e) and (f). Capture probe attachment linkers are indicated by (m) and (n). A99 and A100 are hairpin partial duplex capture probes comprising an attachment linker. A101 and A102 are bi-molecular partial duplex capture probes comprising an attachment linker, wherein the attachment linker is on the strand comprising the variable address portion. A103 and A104 are bi-molecular partial duplex capture probes comprising two attachment linkers (m and n). A105 and A106 are oligonucleotide capture probes comprising attachment linkers. A107 is a dendrimeric capture probe comprising oligonucleotide capture probes (105 and 106). A91 is an immobilized dendrimer particle. B shows types of capture probes immobilized on a solid substrate (B92)—a hairpin capture probe (B99), two bi-molecular partial duplex capture probes (B101 and B103) and an oligonucleotide capture probe (B104). C shows an array of capture probes immobilized to beads. Described is the use of microbeads (a.k.a. micro-partials) as an immobilized substrate for capture probes, wherein a microbead has unique distinguishable characteristics, are pooled into sets or array of sets. C108 is a capture probe immobilized on a microbead with an embedded barcode (U.S. Patent Application 20040075907), wherein a hairpin capture probe (C99) is linked to an encoded bead (C95). C109 is a capture probe immobilized on a microbead with incorporated fluorochromes (U.S. Pat. No. 5,981,180), wherein a hairpin capture probe (C99) is linked to a dye colored bead (C96). D is an embodiment of a polymeric micelle that encapsulates hydrophobic molecules, such as fluorescent dyes and Quantum Dots for example. These polymers are designed with a branched, hydrophobic interior (core) and hydrophilic exterior (shell) to maintain physical properties characteristic of conventional micelles, but with enhanced thermodynamic stability. Capture probes are covalently linked to hydrophilic appendages (also called hydrophilic branches) specific for targeting moieties, wherein the polymeric micelle may be covalently attached to an immobilized substrate via its hydrophilic appendages specific for attachment moieties. D110 is a polymeric micelle comprising hairpin capture probe (D99) linked to the polymeric micelle's hydrophilic branches (D111).

Figure 9:
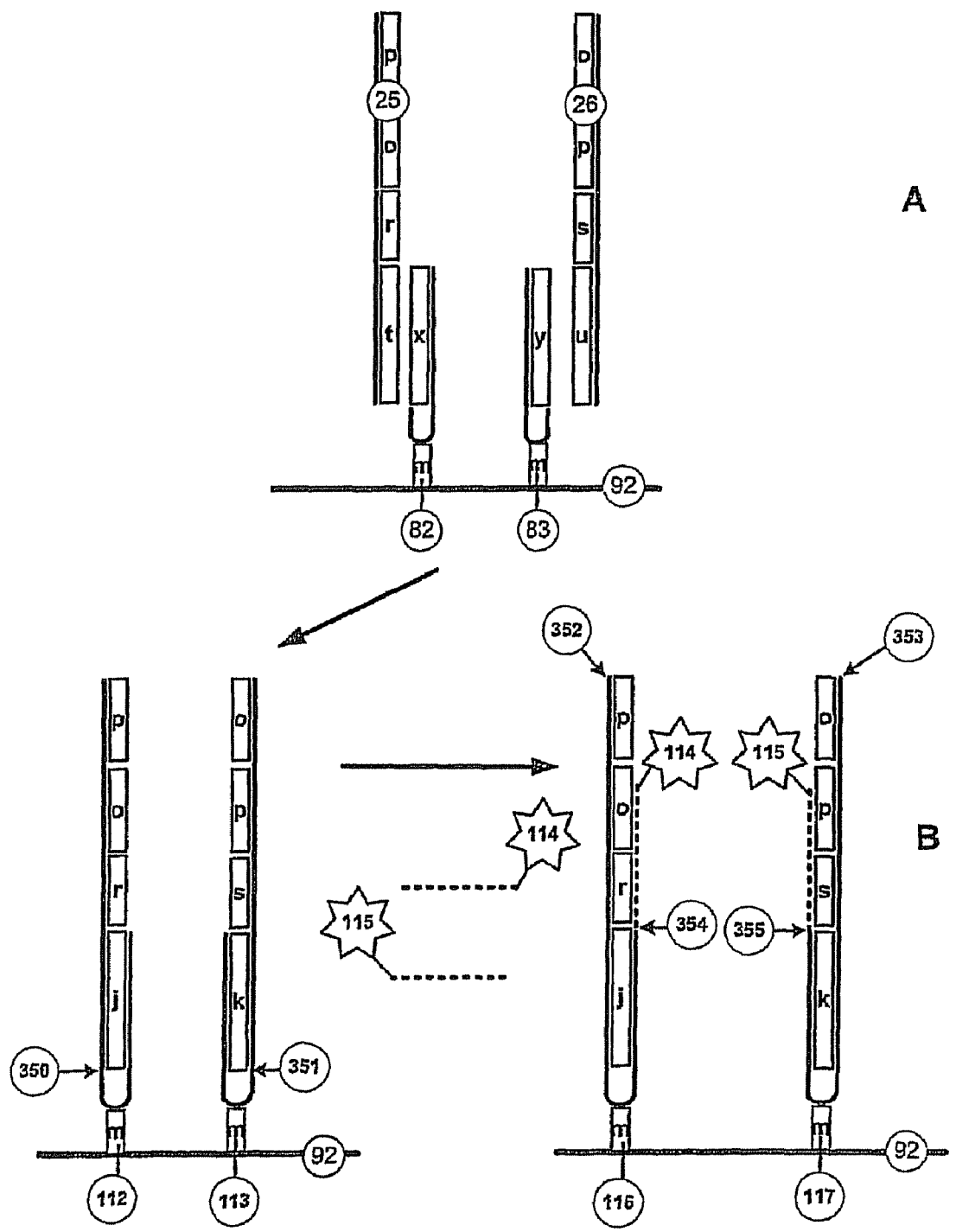
Figure 10:
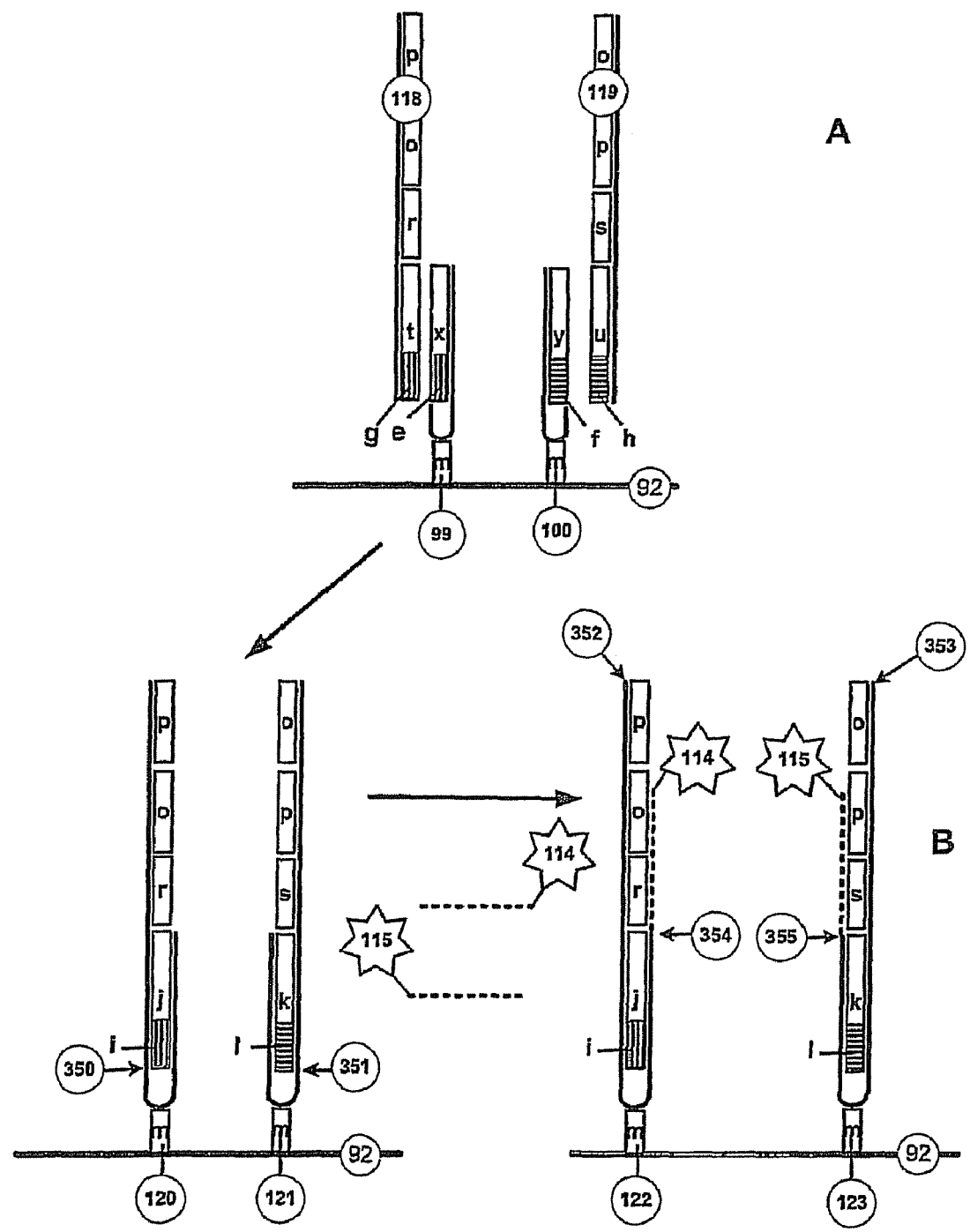

FIGS. 9 and 10 illustrate methods of detecting sequence tag-capture probe hybrids.

FIG. 9 is a schematic representation of an embodiment of the invention's detection phase to produce detectable sequence tag-capture probe hybrids. A shows single stranded (ss) sequence tags comprising complementary sequence portion to the capture probe address portion (the probe variable sequence address). Partial sequence tags, although not shown, form detectable sequence tag-capture probe hybrids as described. A25 and A26 are ss sequence tags comprising primer sites indicated by (o) and (p); cleavable recognition sequences indicated by (r) and (s); and complementary sequence (also referred as cAddress) portions indicated by (t) and (u)—also called target nucleic acid portion. Hairpin capture probes (A82 and A83) are attached, via a linker (m), to the solid substrate (92). The capture probe's variable sequence address portions are indicated by (x) and (y). B shows sequence tag-capture probes hybrids. The design of the detector probe provides many modes of detection. The degree of multiplexing is limited by the number of labels and the state-of-art detection systems. The detection method can employ both linear and hairpin detectors to maximize target signal. Shown is an example of linear oligonucleotide detector probes. Furthermore, shown is the employment of two different label detector probes to survey captured sequence tags. Direct and Indirect detection methods are known in the art. Direct methods include fluorescent dye labels from Molecular Probes, non-fluorescent quenching labels from Epoch, and amplifiable labels such as RCA and antibodies, for example. Indirect methods include fluorescent and mass spectrometry labels with Alcara's eTag reporter system and Quantum Dots, for example. B112 and B113 are sequence tag-capture probe hybrid comprising bi-molecular address portions (j and k) from the hybridization and ligation of A25 (portion t) with A82 (portion x) and hybridization and ligation of A26 (portion u) with A83 (portion y). The ligation sites are indicated by numbers 350 and 351. B114 and B115 are detector probes that are hybridized, ligated, and washed to sequence tag-capture probe hybrids. Produced are detectable sequence tag-capture probe indicated by B116 and B117. The linear detector probe ligation sites are indicated by numbers 354 and 355, and the hairpin detector ligation sites are indicated by numbers 352 and 353. Not shown, but described, is an embodiment that uses hairpin labeled detector probes to survey captured sequence tags.

FIG. 10 is a schematic representation of another embodiment of the invention's detection phase to produce detectable sequence tag-capture probe hybrids, wherein the sequence tag-capture probe hybrid comprises a bi-molecular probe constant address. A shows single stranded (ss) sequence tags comprising complementary sequence portion to the capture probe address portion (the probe variable sequence address). Partial sequence tags, although not shown, form detectable sequence tag-capture probe hybrids as described. Furthermore, subpopulations of capture probes, wherein all capture probes in a subpopulation have a common probe constant address, also called a probe constant sequence (PCS). A118 and A119 are ss sequence tags comprising primer sites indicated by (o) and (p); cleavable recognition sequences indicated by (r) and (s); complementary sequence (cAddress) portions indicated by (t) and (u)—also called target nucleic acid portion; and complementary sequence constant probe sequence portions indicated by (g) and (h). Hairpin capture probes (A99 and A100) are attached, via a linker (m) to the solid substrate (92). The capture probe's variable sequence address portions are indicated by (x) and (y). B shows sequence tag-capture probes hybrids. The design of the detector probe provides many modes of detection. The degree of multiplexing is limited by the number of labels and the state-of-art detection systems. The detection method can employ both linear and hairpin detectors to maximize target signal. Shown is an example of linear oligonucleotide detector probes. Furthermore, shown is the employment of two different label detector probes to survey captured sequence tags. Direct and Indirect detection methods are known in the art. Direct methods include fluorescent dye labels from Molecular Probes, non-fluorescent quenching labels from Epoch, and amplifiable labels such as RCA and antibodies, for example. Indirect methods include fluorescent and mass spectrometry labels with Alcara's eTag reporter system and Quantum Dots, for example. The capture probe's probe constant sequence address are indicated portions (e) and (f). B120 and B121 are sequence tag-capture probe hybrid comprising bi-molecular address portions (j and k) and bi-molecular probe constant sequence portions (i and l) from the hybridization and ligation of A118 with A99 and hybridization and ligation of A119 with A100. The ligation sites are indicated by numbers 350 and 351. B114 and B15 are detector probes that can be hybridized, ligated, and washed. B122 and B123 are detector probes that are hybridized, ligated, and washed to sequence tag-capture probe hybrids. The linear detector probe ligation sites are indicated by numbers 354 and 355, and the hairpin detector ligation sites are indicated by numbers 352 and 353. Not shown, but described, is an embodiment that uses hairpin labeled detector probes to survey captured sequence tags.

FIGS. 11-18 illustrate different detector probes and different methods of detecting sequence tag-capture probe hybrids.

FIG. 11 is a schematic representation of an embodiment of the invention's detection sequence tag-capture probe hybrids, wherein the sequence tag-capture probe hybrids where produced from a capture probe and a single stranded (ss) sequence tag. Illustrated are detector probes coupled to sequence tag-capture probe hybrids, wherein the capture probes are attached by a linker (m) to a solid substrate (92) and the sequence tag-capture probe hybrids comprise a primer site portion, a cleavable recognition site and a bi-molecular address portion. Primer site portions are indicated by (o) and (p). Cleavable recognition sites are indicated by (r) and (s). Bi-molecular address portions are indicated by (j) and (k). Ligation sites for detector probes coupled to the sequence tag-capture probe hybrids are indicated by numbers 352, 353, 354, 355, 365, 366, 367, 368, 369, and 370. Direct and Indirect detection methods are known in the art. Direct method such as fluorescent dye labels and molecular beacons from Molecular Probes; non-fluorescent quenching labels from Epoch; and amplifiable labels such as RCA and antibodies for example. Indirect methods such as eTag reporters (fluorescent, mass spectrometry); EviTags (Quantum Dots) from Evident; and Agilix Corporation's i-Prot mass spectrometry labels for example. A shows sequence tag-capture probe hybrids comprising a single detector probe. A124 and A125 comprise one labeled oligonucleotide detector probe. The detector probes (A126 and A127) contain no complementary portion of the target nucleic acid portion. A128 and A129 comprise one labeled detector probe (A130 and A131), wherein the detector probes contains a complementary portion of the target nucleic acid portion. The target nucleic acid portions are indicated by (t) and (u). A132 and A133 comprise one labeled oligonucleotide hairpin detector probe (A134 and A135). A136 and A137 comprise one labeled oligonucleotide hairpin detector probe with an attachment moiety (A138 and A139). The attachment moiety is indicated by (t). B shows sequence tag-capture probe comprising detector probe multiplexing, wherein two or more detector probes are coupled. B140 and B141 comprise two labeled oligonucleotide detector probes (B142, B143, B144 and B145). B146 and B147 comprise two oligonucleotide detector probes and one hairpin oligonucleotide detector probe. The oligonucleotide detector probes are indicated by B149, B150, B152, and B153. The hairpin oligonucleotide detector probes are indicated by B148 and B151. B154 and B155 comprise one linear oligonucleotide detector probe (B157 and B159) and one hairpin oligonucleotide detector probe (B156 and B158).

FIG. 12 is a schematic representation of another embodiment of the invention's detection sequence tag-capture probe hybrids, wherein the sequence tag-capture probe hybrids where produced from a capture probe and a partial duplex sequence tag. Illustrated is detector probes coupled to sequence tag-capture probe hybrids, wherein the capture probe is attached by a linker (m) to a solid substrate (92) and the sequence tag-capture probe hybrids comprise a primer site portion, a cleavable recognition site, a bi-molecular address portion, and sequence tag-capture probe hybrid ligation sites. Primer site portions are indicated by (o) and (p). Cleavable recognition sites are indicated by (r) and (s). Bi-molecular address portions are indicated by (j) and (k). Complementary sequence (cAddress) portions are indicated by (t) and (u)—also called target nucleic acid portion. Sequence tag-capture probe hybrid ligation sites are indicated by numbers 350, 351, 354, and 355. Ligation sites for detector probes coupled to the sequence tag-capture probe hybrids are indicated by numbers 371, 372, 373 and 374. Direct and Indirect detection methods are known in the art. Direct method such as fluorescent dye labels and molecular beacons from Molecular Probes; non-fluorescent quenching labels from Epoch; and amplifiable labels such as RCA and antibodies, for example. Indirect methods such as eTag reporters (fluorescent, mass spectrometry); EviTags (Quantum Dots) from Evident; and Agilix Corporation's i-Prot mass spectrometry labels, for example. A160, A164, A161, A166, B184 and B186 shows sequence tag-capture probe hybrids comprising a single detector probe. Detector probes are indicated by numbers 162, 163, 165, 167, 169, 171, 173, 174, 177, 176, 179, 180, 182, 183, 185 and 187. Sequence tag-capture probe hybrids indicated by A160, A164, A161, and A166 are comprised of one labeled oligonucleotide detector probe and an oligonucleotide partial duplex sequence tag. Sequence tag-capture probe hybrid indicated by A168 and A170 are comprised of one labeled oligonucleotide detector probe and hairpin partial duplex sequence tag, wherein the detector probe contains no complementary portion of the target portion. Sequence tag-capture probe hybrid indicated by B184 and B180 are comprised of one labeled oligonucleotide detector probe and hairpin partial duplex sequence tag, wherein the detector probe contains a complementary portion to the target nucleic acid portion. The target nucleic acid portions are indicated by (t) and (u). Sequence tag-capture probe hybrid indicated by B172, B178, B175, and B181 are comprised of two labeled oligonucleotide detector probes and a partial duplex sequence tag.

Figure 13:
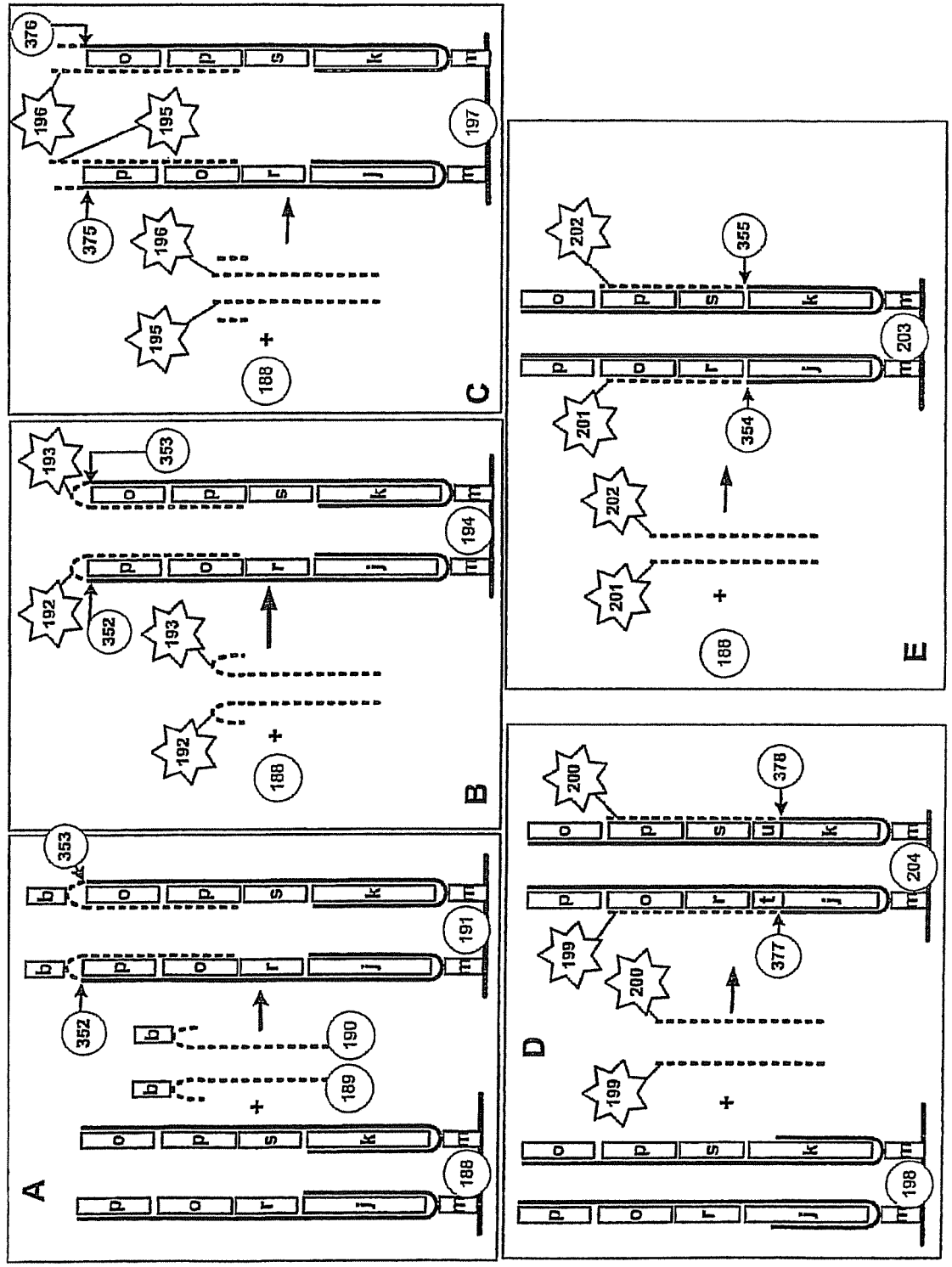

FIG. 13 is a schematic representation of an embodiment of the invention illustrating different methods to produce detection sequence tag-capture probe hybrids, wherein one detector probe is coupled to the sequence tag-capture probe hybrids, wherein the sequence tag-capture probe hybrid comprises a primer site portion, a cleavable recognition site and a bi-molecular address portion, and an attachment linker (m). Primer site portion are indicated by (o) and (p). Cleavable recognition sites are indicated by (r) and (s). Bi-molecular address portions are indicated by (j) and (k). Ligation sites for detector probes coupled to the sequence tag-capture probe hybrids are indicated by numbers 352, 353, 354, 355, 375, 376, 377, and 378. A shows the hybridization and ligation of immobilized sequence tag-capture probe hybrids (188) with a second oligonucleotide hairpin detector probe (A189 and A190) comprising an attachment moiety (i.e.: biotin) to produce detectable sequence tag-capture probe hybrids (A191). The attachment moiety is indicated by (b). B shows the hybridization and ligation of sequence tag-capture probe hybrids (188) with a second labeled oligonucleotide hairpin detector probe (B192 and B193) to produce detectable sequence tag-capture probe hybrids (B194). C shows the hybridization and ligation of sequence tag-capture probe hybrids (188) with a second labeled partial duplex detector probe (C195 and C196) to produce detectable sequence tag-capture probe hybrids (C197). D shows the hybridization and ligation of sequence tag-capture probe hybrids (198) with a first labeled oligonucleotide detector probe (C199 and C200) to produce detectable sequence tag-capture probe hybrids (C204), wherein the detector probe contains a complementary portion of the target nucleic acid portion. The target nucleic acid portions are indicated by (t) and (u). E shows the hybridization and ligation of sequence tag-capture probe hybrids (188) with a first labeled oligonucleotide detector probe (C201 and C202) to produce detectable sequence tag-capture probe hybrids (C203).

Figure 14:
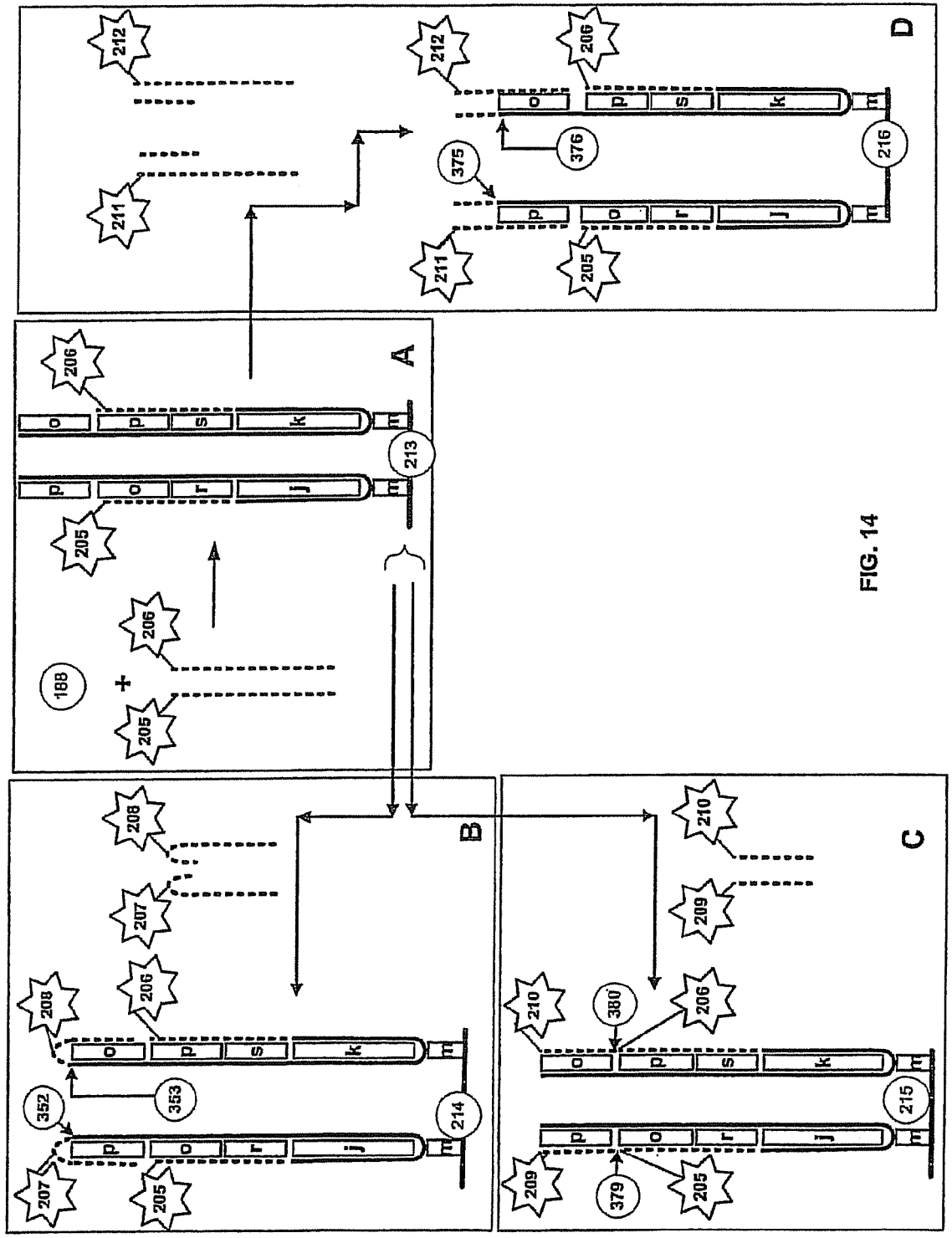

FIG. 14 is a schematic representation of another embodiment of the invention illustrating different methods to produce detection sequence tag-capture probe hybrids, wherein two detector probes are coupled to the sequence tag-capture probe hybrids, wherein the sequence tag-capture probe hybrid comprises a primer site portion, a cleavable recognition site, a bi-molecular address portion, and an attachment linker (m). Primer site portions are indicated by (o) and (p). Cleavable recognition sites are indicated by (r) and (s). Bi-molecular address portions are indicated by (j) and (k). Ligation sites for detector probes coupled to the sequence tag-capture probe hybrids are indicated by numbers 352, 353, 375, 376, 379, and 380. A shows the hybridization and ligation of sequence tag-capture probe hybrids (188) with a first oligonucleotide hairpin detector probes (A205 and A206) to produce detectable sequence tag-capture probe hybrids (A213). B shows the hybridization and ligation of sequence tag-capture probe hybrids (213) with second labeled oligonucleotide hairpin detector probes (B207 and B208) to produce detectable sequence tag-capture probe hybrids (B214). C shows the hybridization and ligation of sequence tag-capture probe hybrids (213) with second labeled oligonucleotide detector probes (C209 and C210) to produce detectable sequence tag-capture probe hybrids (C215). D shows the hybridization and ligation of sequence tag-capture probe hybrids (213) with second labeled partial duplex detector probes (D211 and D212) to produce detectable sequence tag-capture probe hybrids (C216). Another embodiment of detector probes 207, 208, 209, 210, 211 and 212 can comprise a targeting or an attachment moiety; i.e.: biotin. Another embodiment in producing products 214 and 216 uses second labeled detector probes which hybridize and ligate to the first labeled detector probe.

Figure 15:
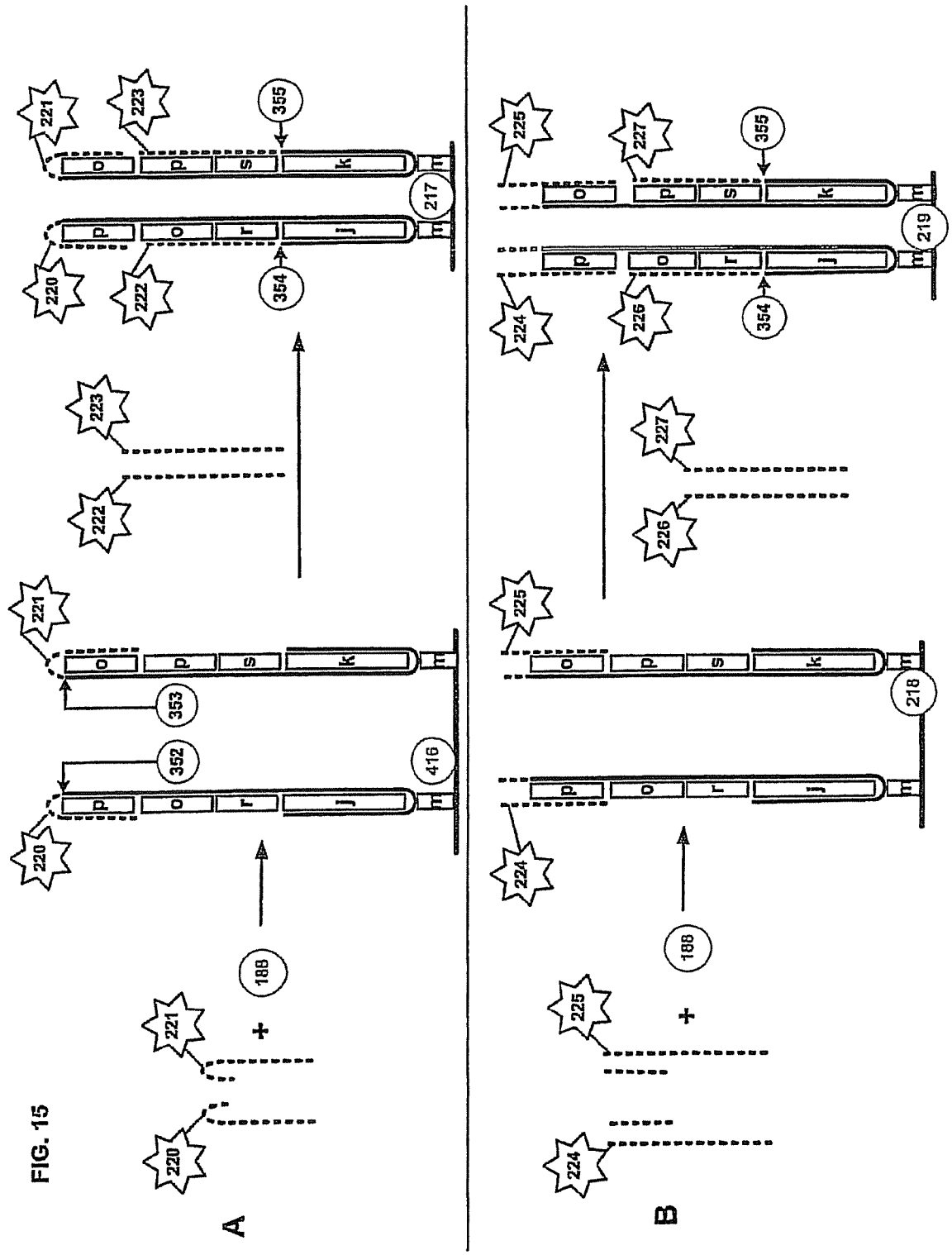

FIG. 15 is a schematic representation of another embodiment of the invention illustrating different methods to produce detection sequence tag-capture probe hybrids, wherein two detector probes are coupled to the sequence tag-capture probe hybrids, wherein the sequence tag-capture probe hybrid comprises a primer site portion, a cleavable recognition site, a bi-molecular address portion, and an attachment linker (m). Primer site portions are indicated by (o) and (p). Cleavable recognition sites are indicated by (r) and (s). Bi-molecular address portions are indicated by (j) and (k). Ligation sites for detector probes coupled to the sequence tag-capture probe hybrids are indicated by numbers 352, 353, 354, and 355. A shows the hybridization and ligation of sequence tag-capture probe hybrids (188) with second labeled hairpin detector probes (A220 and A221) to produce detectable sequence tag-capture probe hybrids (A416). A416 is hybridized and ligated with first labeled oligonucleotide probes (A222 and A223) to produce detectable sequence tag-capture probe hybrids (A217). B shows the hybridization and ligation of sequence tag-capture probe hybrids (188) with second labeled partial duplex detector probes (B224 and B225) to produce detectable sequence tag-capture probe hybrids (B218). B219 is hybridized and ligated with first labeled oligonucleotide probes (A226 and A227) to produce detectable sequence tag-capture probe hybrids (A219). Another embodiment of detector probes 220, 221, 224, and 225 can comprise a targeting or an attachment moiety; i.e.: biotin. Another embodiment in producing products 217 and 219 uses first labeled detector probes which hybridize and ligate to the second labeled detector probe.

Figure 16:
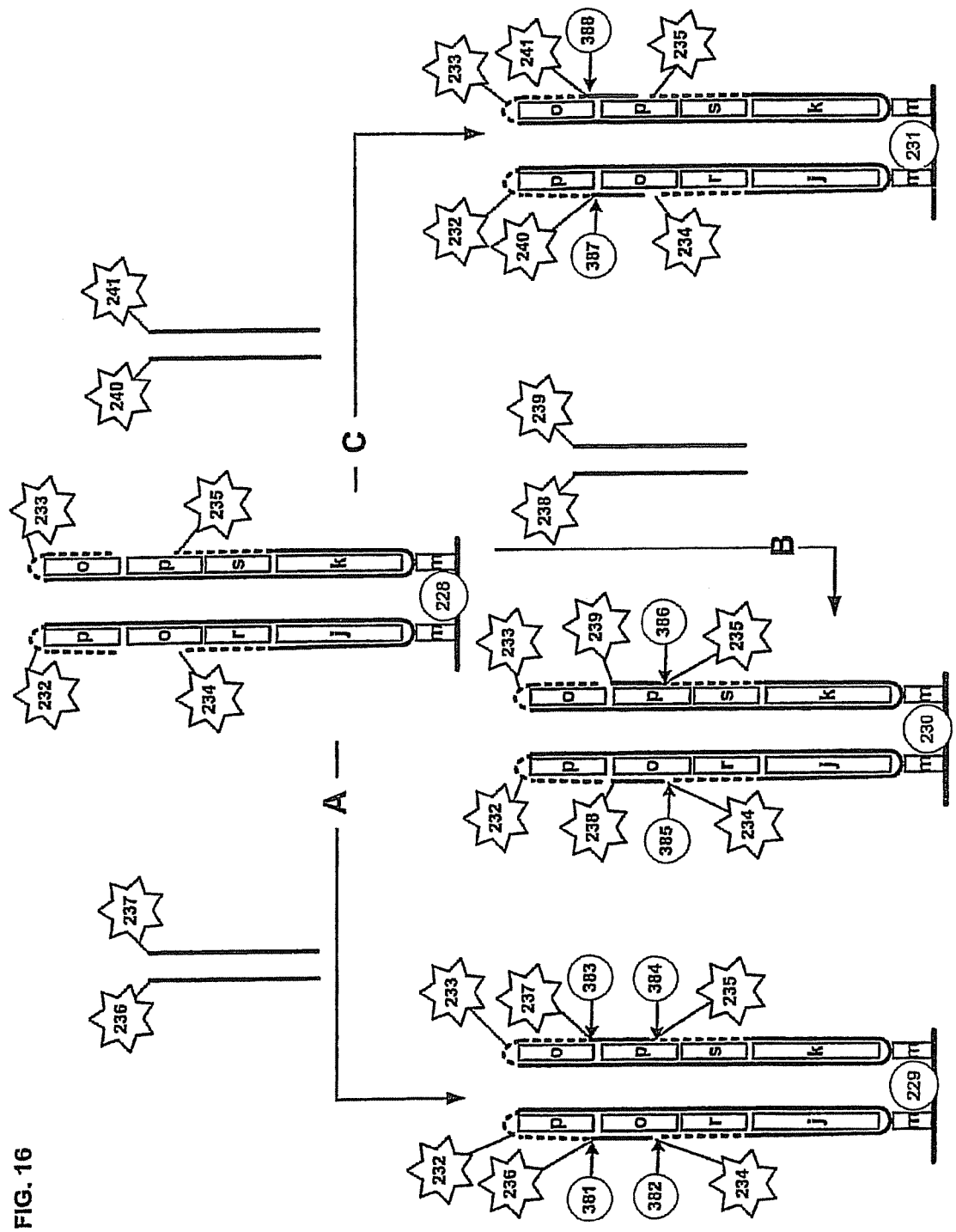

FIG. 16 is a schematic representation of another embodiment of the invention illustrating different methods to produce detection sequence tag-capture probe hybrids, wherein three detector probes are coupled to the sequence tag-capture probe hybrids, wherein the sequence tag-capture probe hybrid comprises a primer site portion, a cleavable recognition site, a bi-molecular address portion, and an attachment linker (m). Primer site portions are indicated by (o) and (p). Cleavable recognition sites are indicated by (r) and (s), bi-molecular address portions are indicated by (j) and (k). Illustrated are different methods to couple third detector probes to sequence tag-capture probe hybrids (228) comprising a first (234 and 235) and second (232 and 233) labeled detector probes. A shows the hybridization and ligation of sequence tag-capture probe hybrids (288) with third labeled oligonucleotide detector probes (A236 and A237) to produce detectable sequence tag-capture probe hybrids (A229), wherein the ligation sites are at both ends of the third detector probe. The ligation sites are indicated by numbers 381, 382, 383, and 384. B shows the hybridization and ligation of sequence tag-capture probe hybrids (228) with third labeled oligonucleotide detector probes (B238 and B239) to produce detectable sequence tag-capture probe hybrids (B218), wherein the ligation sites are between the first and third detector probes. The ligation sites are indicated by numbers 385 and 386. C shows the hybridization and ligation of sequence tag-capture probe hybrids (228) with third labeled oligonucleotide detector probes (C240 and C241) to produce detectable sequence tag-capture probe hybrids (C231), wherein the ligation sites are between the second and third detector probes. The ligation sites are indicated by numbers 387 and 388. Detector probes 236, 237, 238, 239, 240 and 241 can comprise a targeting or an attachment moiety; i.e.: biotin.

Figure 17:
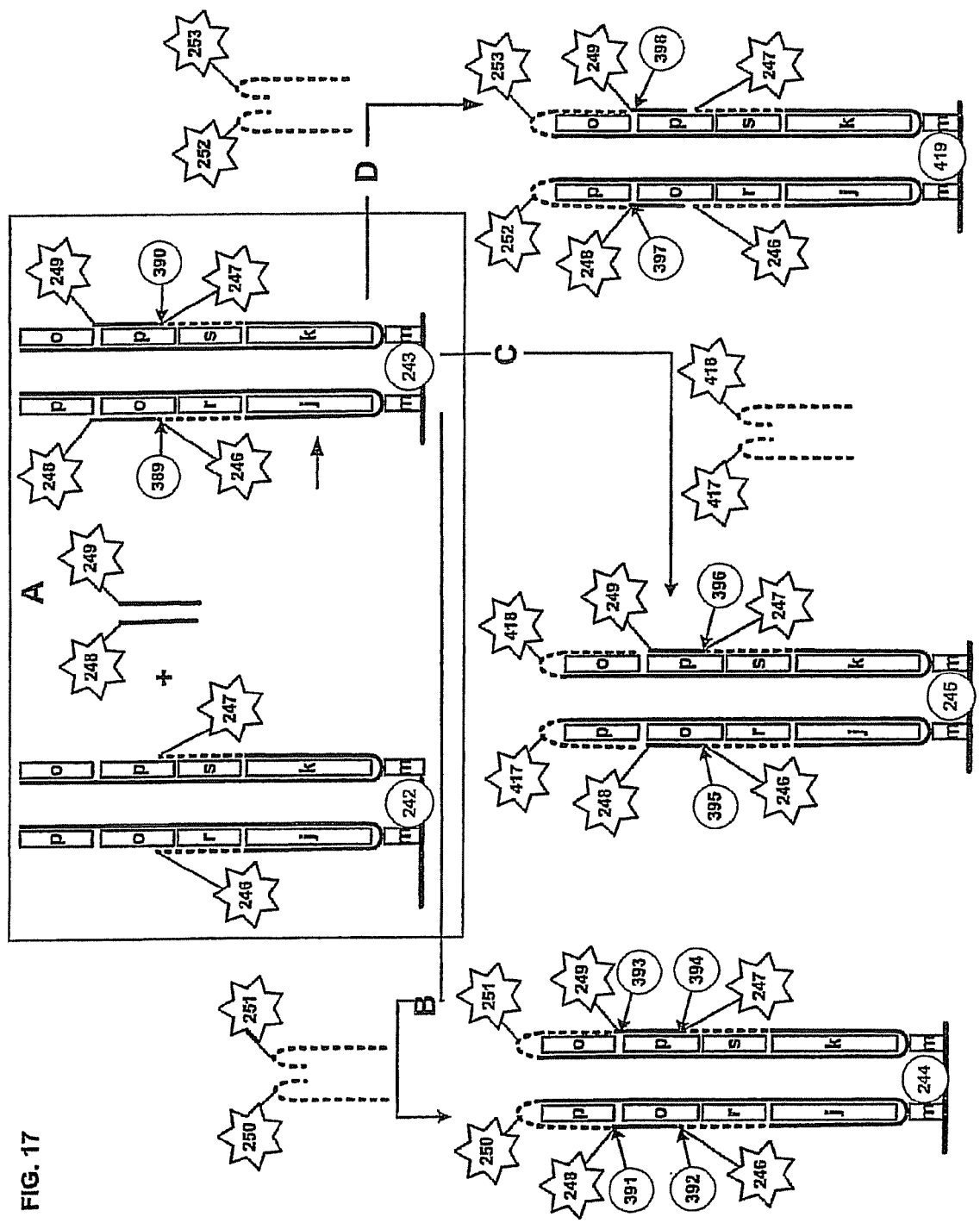

FIG. 17 is a schematic representation of another embodiment of the invention illustrating different methods to produce detection sequence tag-capture probe hybrids, wherein three detector probes are coupled to the sequence tag-capture probe hybrids, wherein the sequence tag-capture probe hybrid comprises a primer site portion, a cleavable recognition site, a bi-molecular address portion, and an attachment linker (m). Primer site portions are indicated by (o) and (p). Cleavable recognition site are indicated by portions (r) and s). Bi-molecular address portions are indicated by (j) and (k). A shows the hybridization and ligation of sequence tag-capture probe hybrids (242), which comprises detector probes (A246 and A247), with third labeled oligonucleotides detector probes (A248) and (A249) to produce detectable sequence tag-capture probe hybrids (A243). B shows the hybridization and ligation of sequence tag-capture probe hybrids (243) with second labeled hairpin detector probes (B250 and B251) to produce detectable sequence tag-capture probe hybrids (B244). The ligation sites are indicated by numbers 391, 392, 393 and 394. C shows the hybridization and ligation of sequence tag-capture probe hybrids (243) with second labeled hairpin detector probes (B417 and B418) to produce detectable sequence tag-capture probe hybrids (B245). The ligation sites are indicated by numbers 395 and 396. D shows the hybridization and ligation of sequence tag-capture probe hybrids (243) with second labeled hairpin detector probes (D252 and D252) to produce detectable sequence tag-capture probe hybrids (D419). The ligation sites are indicated by numbers 397 and 398. Other embodiments substitute suitable second detector probe for the labeled hairpin detector probes indicated by numbers 250, 251, 252, 253, 417 and 418. For example, detector probes 250, 251, 252, 253, 417 and 418 can comprise a targeting or an attachment moiety; i.e.: biotin.

Figure 18:
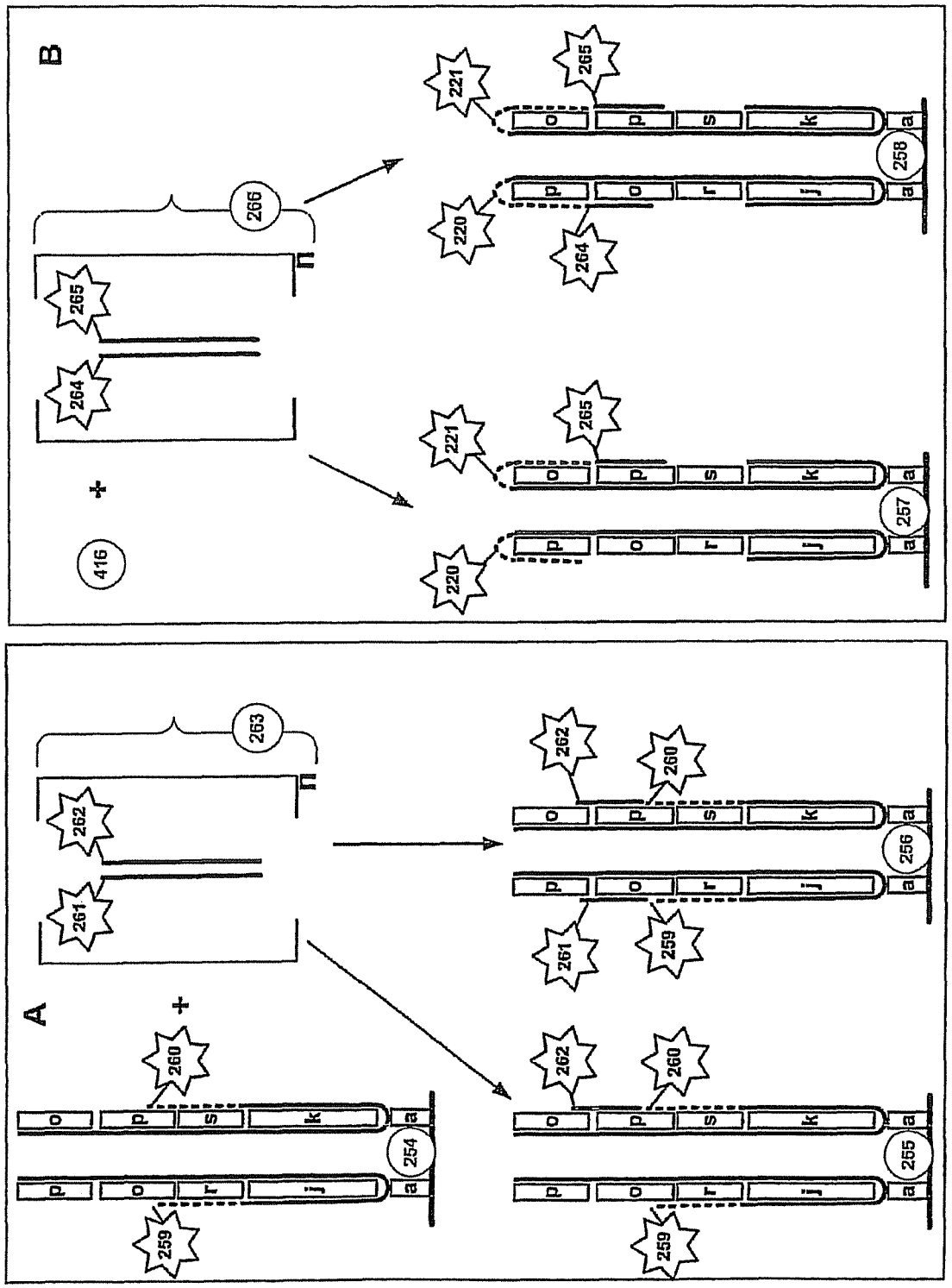

FIG. 18 is a schematic representation of an embodiment of the invention illustrating generalized methods to produce detectable sequence tag-capture probe hybrids, wherein one or more detector probes are coupled to the sequence tag-capture probe hybrids, wherein the sequence tag-capture probe hybrid comprises a primer site portion, a cleavable recognition site, a bi-molecular address portion, and an attachment linker (m). Primer site portions are indicated by (o) and (p). Cleavable recognition site are indicated by portions (r) and (s). Bi-molecular address portions are indicated by (j) and (k). A shows sequence tag-capture probe hybrids coupled with one or more sets of labeled oligonucleotide detector probes. A generalized set number is indicated by (n). Shown is one detector probe set A263 from (n) possibilities, wherein the detector probes are indicated by numbers 261 and 262. A255 and A256 are produced by hybridizing and ligating sequence tag-capture probe hybrids (A254) with detector probes set (A263). B shows one detector probe set A266 from (n) possibilities, wherein the detector probes are indicated by numbers 264 and 265. A257 and A258 are produced by hybridizing and ligating sequence tag-capture probe hybrids (B416) with detector probes set (A266), wherein sequence tag-capture probe hybrids comprise a second hairpin detector probes indicated by numbers 220 and 221.

FIG. 19 illustrates different embodiments of first, second, and subsequent bridges.

FIG. 19 illustrates different embodiments of first, second, and subsequent bridges. Described are example bridges, wherein the bridge specification (also called a schema) comprises a variety of motifs such as offset cleavable recognition sites, bridge with stick ends, amplification primer sites, and attachment moiety, for example. Offset cleavable recognition motifs comprise a bridge's sticky end and/or comprise no portion of a bridge's stick end, wherein the motif is adjacent to a sticky end, offset from the stick end, or combination thereof. Offset cleavable recognition motifs comprise recognition sites for restriction enzyme (RE) systems such as Type IIS, Type III, and Type II subtypes, for example. An embodiment of a bridge comprising a Type IIS recognition motifs, the sites are unique, repeated, or both. An embodiment of a bridge comprising a Type III or Type II subsystem recognition site is unique, wherein the site comprises a nested Type II recognition site. An embodiment of a bridge comprising a sticky end, the sticky ends have complementary sequences. Another embodiment of a bridge comprising a sticky ends, the sticky ends are not complementary sequences. An embodiment of a bridge comprising forward and reverse amplification primer sites, wherein the top and bottom strands have the same primer sequences. Another embodiment of a bridge comprising forward and reverse amplification primer sites, wherein the top and bottom strands have different primer sequences. An embodiment of a bridge comprising an attachment moiety, wherein the moiety is a biotinylated hairpin—also called a loop or bulge. Another embodiment of a bridge comprising an attachment moiety, wherein the moiety is an activated linker available to react with a removing agent. Example of removing agents include activated magnetic bead and activated magnetic particles. An embodiment of a bridge schema enables the method to control sequence tag complexity. Another embodiment of a bridge schema enables the method to classify allele specific tags from genomic DNA. A shows different bridge designs. A504 is a bridge comprised of two Type IIS recognition sites (A500 and A503) and two primers (A501 and A502). A506 is a bridge comprised of two Type IIS recognition sites (A500 and A503) and one Type II recognition site (A505). A510 is a bridge comprising one Type III (A511) and one Type II recognition site (A508), wherein the Type III recognition sequence has two known sequence portions flanking an ambiguous portion. The two known portions are indicated by numbers 507 and 509. B illustrates a bridge specification, comprising a set of motifs. The motif number is indicated by (n). B515 is a generic bridge, wherein B512 indicates one or more 5'-end most motifs, B514 indicates one or more 3'-end most motifs, and B513 indicates one or more motifs flanked by 5'-end most motifs (B512) and 3'-end most motifs (B14). C illustrates bridges comprising a loop motif C520 is a bridge comprising a loop motif with an attachment moiety (C524), two Type IIS recognition sites (C516 and C519), and two primer sites (C517 and C518). C523 is a bridge comprising a loop motif with an attachment moiety (C525) and two primer sites (C521 and C522). The attachment moiety is indicated by (a).

DETAILED DESCRIPTION

Definitions

Nucleic Acid: A nucleic acid is a biological molecule composed of a chain of covalently linked nucleotides. A single-stranded nucleic acid is an unpaired nucleic acid strand. A double-stranded nucleic acid comprises two single-stranded nucleic acids hydrogen-bonded together. The two strands of a double-stranded nucleic acid are complementary, i.e., capable of hydrogen bonding. Typically, A and T (or U in the case of RNA) and G and C nucleotides for base-pairs in a double-stranded nucleic acid. Sticky ends are single-stranded nucleic acid segments at one or both ends of a double-stranded nucleic acid segment. Double-stranded nucleic acid segments comprising compatible sticky ends are capable of concatenation by coupling. A partial duplex nucleic acid is a nucleic acid having a region of double-stranded nucleic acid and at least one region of single-stranded nucleic acid, typically at an end of the molecule. Typically, the single-stranded nucleic acid of a partial duplex nucleic acid comprises greater than or equal to about 4 nucleotides, and is capable of forming thermodynamically stable nucleic acid duplex structure when contacted with a complementary single-stranded nucleic acid. A hairpin duplex is a region of single stranded nucleic acid that folds back on itself to form a double helix. Unlike a partial duplex, a hairpin comprises a contiguous nucleic acid strand.

Nucleic acid sample: Examples of suitable nucleic acid samples include, for example, genomic samples, mRNA samples, cDNA samples, nucleic acid libraries (including cDNA and genomic libraries), whole cell samples, environmental samples, culture samples, tissue samples, bodily fluids, and biopsy samples. Numerous other sources of nucleic acid samples are known or can be developed and can be used with the disclosed methods. Suitable nucleic acid samples for use with the disclosed method include nucleic acid samples of significant complexity such as genomic samples, RNA samples, mRNA samples and cDNA samples.

Target nucleic acid: Target nucleic acids include those produced from a nucleic acid sample. Suitable target nucleic acids include those comprising a 5' sticky end, a 3'sticky end, or a combination thereof. The ends of a target nucleic acid may be produced, for example, by employing a cleaving agent. Examples of suitable cleaving agents for production of target nucleic acids include restriction enzymes of class type: Type II, Type IIS, Type III, Type IIB, or a combination thereof.

Target nucleic acid portion: A target nucleic acid portion is a segment of a sequence tag comprising 2 to 30 nucleotides in length. The target nucleic acid portion comprises sequence from a nucleic acid sample. The target nucleic portion may also comprise an addressable portion.

Primer: Primers are oligonucleotides used to amplify sequence tags, for example. Primers include sequences complementary to one of the strands of a sequence tag, such as a portion of a nucleic acid bridge. The sequence to which a primer hybridizes is referred to as a primer binding site. This sequence is also referred to as the complementary portion of the primer. The complementary portion of primer can be a length that supports specific and stable hybridization between the primer and the primer complement portion. Generally this is 10 to 35 nucleotides long, but may be 16 to 20 nucleotides long. Primers do not have to be 100% complementary to their binding site so long as a stable hybrid can be formed at the operating temperature. Primers can also contain additional sequence at the 5' end of the primer that is not complementary to any part of the sequence tag. This sequence is referred to as the non-complementary portion of the primer. The non-complementary portion of the primer is generally 1 to 100 nucleotides long. Primers need not be entirely single-stranded, but can contain a hairpin region formed between the 5' terminus and an internal sequence in the primer. Such amplification primers are referred to herein as hairpin primers.

A primer may also include modified nucleotides to make it resistant to exonuclease digestion or for other purposes. For example, the primer can have three or four phosphorothioate linkages between nucleotides at the 5' end of the primer.

Hybridization: Hybridization is the attachment by base-pairing (i.e., hydrogen bonding) of two complementary nucleic acid strands. By complementary, it is meant that two nucleic acid strands share sufficient homology (i.e., similarity) to hybridize under the operating conditions. Complementary is not meant to necessarily imply 100% complementarity, although this is possible. Hybridization of a single stranded probe to a longer sequence of DNA may be employed to determine where the complement of the probe resides in the longer sequence.

Stacking hybridization: Stacking hybridization reactions are those in which two or more short DNA oligomers align in a contiguous tandem orientation against a longer complementary DNA single strand, whereby one or more of the oligomers hybridizes to the longer complementary DNA single strand. The molecules produced by stacking hybridization can be employed to enhance a variety of analytical oligonucleotide hybridization schemes. Additional stability can be associated with DNA hybridization reactions wherein two or more DNA oligomers hybridize in a contiguous tandem arrangement to a longer complementary DNA single strand.

Short DNA oligomers that participate in the reaction may be the single stranded portion of a partial DNA duplex or DNA hairpin having a single strand dangling end.

Coupling: Coupling refers to a joining of nucleic acids strands. The term coupling includes both hybridization and covalent coupling.

Cleaving agent: Nucleic acid cleaving agents are compounds, complexes, and enzymes that cause, mediate, or catalyze cleavage on nucleic acid molecules. Suitable nucleic acid cleaving agents are those that cleave nucleic acid molecules in a sequence-specific manner. Restriction endonucleases (also referred to as Restriction enzymes) are one form of nucleic acid cleaving agents.

Nucleic acid cleaving agents generally have a recognition sequence and a cleavage site. Many nucleic acid cleaving agents, especially restriction enzymes, also generate sticky ends at the cleavage site. A recognition sequence is the nucleotide sequence, which, if present in a nucleic acid molecule, will direct cleavage of the nucleic acid molecule by a cognate nucleic acid cleaving agent. The cleavage site of a nucleic acid cleaving agent is the site, usually in relation to the recognition sequence, where the nucleic acid cleaving agent cleaves a nucleic acid molecule. Sticky ends (also referred to as cohesive ends, protruding ends, and 5' or 3' overhangs) are single-stranded nucleic acid segments at the end of a double-stranded nucleic acid segment.

Type II enzymes cut DNA at defined positions close to or within their recognition sequences. Type II R-M system enzymes recognize nucleotide palindromes of 4 to 8 base pairs in length, interrupted palindromes with some unspecific nucleotides between flanking nucleotides, or partially palindromic sequences with ambiguous nucleotides at certain positions. For most nucleotide sequences, more than one enzyme is available that recognizes that sequence. Type IIS enzymes cleave outside of their recognition sequence to one side, that is, the recognition sequence is offset from the cleavage site. Type III restriction enzymes cleave outside of their recognition sequences and require two such sequences in opposite orientations within the same DNA molecule to accomplish cleavage. The recognition sequences of Type II and Type III enzymes may have ambiguous (i.e., also called variable or unspecified) bases within their recognition sequences. For example, Bgl I recognizes the sequence GCCNNNNNGGC (SEQ ID NO:1), wherein N can be any nucleotide. One of ordinary skill in the art can select a suitable type and subtype of enzyme to accomplish a desired cleavage.

Where a nucleic acid cleaving agent cleaves at a site different or offset from the recognition sequence, a variety of sticky ends having different sequences can be generated. This is because recognition sequences in nucleic acids can occur next to any sequence and therefore the site of cleavage can have any sequence. For example, FokI cleaves 9 (upper strand) and 13 (lower strand) nucleotides downstream from the recognition site of GGATG. The four base sticky end will have whatever sequence happens to be 10 to 13 nucleotides away from the recognition site. Given enough cleavage sites, a total of 256 different sticky end sequences (that is every possible four base sequence) can result from a FokI digestion. As a result, restriction enzymes such as Type IIS restriction enzymes can generate sticky ends having a plurality of different sequences.

As used herein, unless otherwise indicated, the terms digest, digestion, digested, and digesting refer generally to a cleavage reaction or the act of cleaving and is not intended to be limited to cleavage by a protein enzyme or by any particular mechanism. Similarly, the term restricted is intended to refer to any nucleic acid cleavage, not just cleavage by a restriction enzyme. In the context of nucleic acid cleaving reagents, sequence-specific requires only some sequence specificity, not absolute sequence specificity. That is, nucleic acid cleaving agents having a completely or partially defined recognition sequence are preferred. Thus, nucleic acid cleaving reagents having some degeneracy in their recognition sequence are still considered sequence-specific.

First, second and subsequent nucleic acid bridge: As used herein, a bridge is a nucleic acid at least a portion of which is double stranded to which a first target nucleic acid and a second target nucleic acid can be attached at a first end and a second end, respectively. The double-stranded portion has a length sufficient to remain double-stranded under ordinary conditions used for annealing and amplification, for example. The bridge may comprise a branched portion so long as at last a portion of the bridge is double-stranded. The sequence of a first, second or subsequent nucleic acid bridge is variable and may be engineered depending upon the use. A first, second or subsequent nucleic acid bridge may comprise one or more recognition sites for one or more nucleic acid cleaving agents. A first, second or subsequent nucleic acid bridge may also comprise one or more primer binding sites. A first, second or subsequent nucleic acid bridge may also comprise a stem loop, a bulge, an aptamer or combination thereof. A first, second or subsequent nucleic acid bridge may comprise one or more modified nucleic acid bases. Suitable modified bases include, for example, deoxyinosine, deoxyuridine, Fluorescein-dT, TAMRA-dT, Biotin-TEG, Biotin-dT, degenerate bases, or a combination comprising one or more of the foregoing modified bases. FIG. 19 illustrates several examples of nucleic acid bridges.

Linear chimeric nucleic acid intermediate: A linear chimeric nucleic acid intermediate comprises a nucleic acid bridge flanked on either side by a covalently attached target nucleic acid, wherein the ends of the molecule are not joined together, i.e., free.

Shortened linear chimeric nucleic acid intermediate: A shortened linear chimeric nucleic acid intermediate is a portion of a linear chimeric nucleic acid intermediate comprising a first bridge, a first target nucleic acid comprising 2 to 30 nucleotides and a second target nucleic acid comprising 2 to 30 nucleotides. A shortened linear chimeric nucleic acid intermediate includes a linear chimeric nucleic acid bridge in which one or more ends have been treated with a cleaving agent, thus reducing the length of the linear chimeric nucleic acid intermediate.

Modified linear chimeric nucleic acid intermediate: A modified linear chimeric nucleic acid intermediate comprises a second nucleic acid bridge flanked on either side by a covalently attached portion of a shortened linear chimeric nucleic acid intermediate, wherein the shortened linear chimeric nucleic acid intermediate portion is a hybrid comprising at least a portion of a first nucleic acid bridge and at least a portion of a target nucleic acid.

Sequence Tag: A sequence tag is single-stranded or double-stranded nucleic acid sequence comprising a first and/or second nucleic bridge portion and a target nucleic acid portion, wherein the target nucleic acid portion may have an addressable portion. Sequence tags may be double-stranded, single-stranded, partial duplex, or a combination thereof. Sequence tags are detectable by polymerase chain reaction (PCR), for example. The target nucleic acid portion of a sequence tag may have a portion having an occurrence in a genome and whose location and base sequence is known. There are thousands of genomes stored in the NCBI Entrez Genome repository, for example, genomes for bee, cat, chicken, cow, dog, frog, fruit fly, human, malaria parasite, mosquito, mouse, nematode, pig, rat, sea urchin, sheep, zebrafish, thale cress, tomato, rice, oat, soybean, barley, bread wheat, corn, over 1000 viruses and over 100 microbes. A sequence-specific portion of the target nucleic portion determined by the disclosed method may be employed to identify an occurrence in a genome. For example, querying the NCBI Entrez Genome repository with the sequence-specific portion may result with a least one occurrence. Furthermore, a single occurrence from several organisms may be a portion of a putative ortholog.

Addressable Portion: The addressable portion of a sequence tag is the portion that allows binding or capture of the sequence tag by a complementary capture probe. The addressable portion of the sequence tag is that portion that hybridizes with a capture probe. The addressable portion of a sequence tag comprises a complement address (cAddress), a complement probe constant sequence (cPCS), or a combination thereof. The complement address is unique to a particular sequence tag, while the complement probe constant sequence is shared by at least a subset of sequence tags.

Capture Probe: A capture probe is comprises a polynucleotide that binds selectively to a nucleic acid sequence of interest, and which can be immobilized on a substrate or coupled to a fluidic material, such as a polymeric micelle. A capture probe may comprise an attachment portion suitable for attachment of the capture probe to a support. A capture probe can capture a sequence tag by hybridizing, preferably by stacking hybridization, to the sequence tag and thereby immobilizing it. A capture probe includes one strand that is substantially complementary to a portion of the sequence tags. A hairpin capture probe is a capture probe which comprises two mutually complementary nucleic acid regions such that at least one intramolecular duplex may be formed as described in U.S. Pat. No. 5,770,365. A capture polymer is a capture probe which comprises branched multimers which are highly complex polynucleotides that comprise a polynucleotide backbone having multifunctional nucleotides, each of which defines a sidechain site and a single-stranded oligonucleotide unit that is capable of binding to a polynucleotide of interest as. Examples are described in U.S. Pat. Nos. 5,849,481; 5,624,802; 5,710,264 and 5,124,246; and U.S. Patent Application No. 20040009506.

The capture probe has an addressable portion which may comprise a probe address (Address), a probe constant sequence (PCS) or a combination thereof. These sequences are complementary to the complement probe address (cAddress), the complement probe constant sequence (cPCS) or combination thereof, of the sequence tag.

Capture probes may include sets having a variety of probe sequences, including a set of probes having every possible combination (or hybridizable to every combination) of nucleotide sequence the length of the probe. Capture probes may include sets where each probe has the same length. Suitable lengths for the Address portion of capture probes are 5 to 70 nucleotides, for example. Capture probes may include a single-stranded portion (for hybridization to sequence tags) and a linker portion through which the attachment portion can be coupled to a substrate, for example. The linker portions have a suitable structure and may be chosen based on the method of immobilization or synthesis of the capture probes. The linker portion can be made up of, or include nucleotides, for example. The linker portions can have a suitable length to allow the probe portion to hybridize effectively. In one embodiment, capture probes are partial duplexes to promote stacking hybridization with a sequence tag. For convenience and unless otherwise indicated, reference to the length of capture probes may refer to the length of the single-stranded portion of the capture probes. Immobilized capture probes are immobilized on a support.

Capture probes can be immobilized on a support, wherein immobilization is facilitated by coupling wherein a support can be a substrate or can be a fluidic materials such as polymeric micelles, for example. Capture probes can also contain or be associated with sorting labels to facilitate sorting or separation of the sequence tag-capture probe hybrids to which they have been coupled. Detector probes can also contain or be associated with labels to facilitate detection of the capture probes and to which they have been coupled.

Capture probes can also include one or more photocleavable nucleotides to facilitate release of probe sequences coupled to the probe.

Capture probes can also include one or more mass labels to facilitate detection of the capture probes and to which they have been coupled.

Reagent suitable to reduce reactivity: A reagent suitable to reduce reactivity (also called a blocker or a blocking agent) may be a nucleic acid that hybridizes to nucleic acid and prevents the nucleic acid from further reaction.

For example, a hairpin or partial duplex nucleic acid complementary to at least a portion of a nucleic acid target may be employed to prevent a target nucleic acid from reaction (i.e., deactivate undesired target nucleic acids in producing sequence tags).

In another example, a hairpin or partial duplex nucleic acid complementary to at least a portion of a first and/or second nucleic acid bridge may be employed to prevent excess bridge from reaction (i.e., deactivate the excess bridge).

In yet another example, a hairpin or partial duplex nucleic acid complementary to at least a portion of a sequence tag may be employed to prevent a sequence tag, single-stranded and/or partial duplex from reaction (i.e., deactivate undesired sequence tag in being captured).

Labels: To aid in detection and quantitation of sequence tags and sequence tag-capture probe hybrids, coupled to detector probes, labels can be incorporated into, coupled to, or associated with, capture probes, detector probes, and/or sequence tags. A label is a molecule that can be associated with a nucleic acid, directly or indirectly, and which results in a measurable, detectable signal, either directly or indirectly. A label is associated with a component when it is coupled or bound, either covalently or non-covalently, to the component. Many suitable labels for incorporation into, coupling to, or association with nucleic acid are known. Examples of labels suitable for use in the disclosed method are biotin, radioactive isotopes, fluorescent molecules, phosphorescent molecules, bioluminescent molecules, enzymes, antibodies, fluorescent semiconductor nanocrystals (also known as Quantum Dots), molecular beacons, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylindole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Suitable fluorescent labels for simultaneous detection are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, Oreg. and Research Organics, Cleveland, Ohio.

Other labels include molecular or metal barcodes, mass labels, and labels detectable by nuclear magnetic resonance, electron paramagnetic resonance, surface enhanced raman scattering, surface plasmon resonance, fluorescence, phosphorescence, chemiluminescence, resonance raman, microwave, or a combination thereof. Mass labels are compounds or moieties that have, or which give the labeled component, a distinctive mass signature in mass spectroscopy. Mass labels are useful when mass spectroscopy is used for detection. Suitable mass labels are peptide nucleic acids and carbohydrates. Other suitable mass labels include isobaric mass labels, wherein upon fragmentation, each label has a unique mass signature, wherein prior to fragmentation, isobaric labels are isolated.

Combinations of labels can also be useful. For example, color-encoded microbeads having hundreds of distinguishable colors are commercially available. 256 unique combinations of labels, are useful for distinguishing numerous components. For example, 256 different detector probes can be uniquely labeled and detected allowing multiplexing and automation of the disclosed method.

Metal barcodes, a form of molecular barcode, are 30-300 nm diameter by 400-4000 nm multilayer multi metal rods. These rods can be constructed by electrodeposition into an alumina mold, then the alumina is removed leaving these small multilayer objects behind. The system can have up to 12 zones encoded, in up to 7 different metals, where the metals have different reflectivity and thus appear lighter or darker in an optical microscope depending on the metal; this leads to practically unlimited identification codes. The metal bars can be coated with glass or other material, and probes attached to the glass using methods commonly known in the art; assay readout is by fluorescence from the target, and the identity of the probe is from the light dark pattern of the barcode.

Molecular beacons are single-stranded oligonucleotide hybridization probes that form a stem-and-loop structure. The loop contains a probe sequence that is complementary to a target sequence, and the stem is formed by the annealing of complementary arm sequences that are located on either side of the probe sequence. A fluorophore is covalently linked to the end of one arm and a quencher is covalently linked to the end of the other arm. Molecular beacons do not fluoresce when they are free in solution. However, when they hybridize to a nucleic acid strand containing a target sequence they undergo a conformational change that enables them to fluoresce brightly.

Quantum Dots (QDots) are nanometer (10-9 meter) scale semiconductor nanocrystal particles. Their composition and small size is the order of a few hundred to a few thousand atoms. The anatomy of a QDots absorb light, then quickly re-emit the light but in a different color. Quantum dots exhibit the fluorescence phenomenon, fluorophores that are be bright and non-photobleaching with narrow, symmetric emission spectra, and have multiple resolvable colors that can be excited simultaneously using a single excitation wavelength. Examples of QDots include nanocrystals composed of semiconductor material such as cadmium sulfide (CdS), cadmium selenide (CdSe), or cadmium telluride (CdTe). The semiconductor material used to form a QDot nanocrystal is chosen based upon the emission wavelength range being targeted.

Substrate: Substrates for use in the disclosed method can include a solid material to which components of the assay can be adhered or coupled. Examples of substrates include, but are not limited to, materials such as acrylamide, cellulose, nitrocellulose, glass, silicon, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Substrates can have a useful form including thin films or membranes, beads, bottles, dishes, fibers, woven fibers, shaped polymers, particles and microparticles. Suitable forms of substrates include plates and beads.

Bead: A bead is a small substantially spherical substrate suitable for attachment of capture probes, for example. Suitable beads include magnetic beads, dendrimer beads, beads comprising a molecular barcode and beads comprising a fluorophore.

Polymeric micelle: A polymeric micelle is a branched polymer comprising a hydrophobic reporter agent and an amphiphilic block copolymer, wherein a targeting moiety, a capture probe, an attachment moiety, or combination thereof, is covalently attached to a hydrophilic polymer segment. Polymeric micelles have a hydrophobic interior (core) and hydrophilic exterior (shell) to maintain physical properties characteristic of conventional micelles, but with enhanced thermodynamic stability. Polymeric micelles are fluidic self-assembled materials that can change shape and/or size as a function of temperature, salinity, pH or surfactant concentration, for example. Polymeric micelles may be self-assemblies of amphiphilic block copolymers or a cross-linked polymeric network comprised of monomers. Polymeric micelles can have all the functionality of a support or substrate suitable for the disclosed method. Examples of suitable polymeric micelles are described, for example, in U.S. Pat. Nos. 6,497,895 6,521,736, 6,730,334, 6,884,842, and U.S. Patent Applications 20040058006 and 20040198641. Polymeric micelles are in a general class of materials known as micro-particles.

The hydrophobic polymer segment of a polymeric micelle may comprise one or more hydrophobic reporter agents such as a semiconductor nanoparticle, a photochromic dye, a light imaging contrast agent, a fluorescent dye, a mass label, or a combination comprising one or more of the foregoing.

A polymeric micelle may comprise an attachment moiety coupled to the hydrophilic polymer segment, wherein the attachment moiety facilitates immobilization to a substrate Hydrophobic reporter agent: To aid in detection and quantitation of polymeric micelles, hydrophobic reporter agents can be incorporated into, coupled to, or associated with the hydrophobic polymer segment of a polymeric micelle. A hydrophobic reporter agent is bound, either covalently or non-covalently, to the hydrophobic polymer segment. Many suitable hydrophobic reporter agents for incorporation into, coupling to, or association with polymeric micelles are known. Furthermore, hydrophobic reporter agents can be combined, resulting in thousands of additional color possibilities. Examples of suitable reporter agents include photochromic dyes such as Photosol Photochromic Dyes from PPG and Quantum Dots such as EviDots from Evident Technologies, semiconductor nanocrystals such as those described in U.S. Pat. No. 6,319,426 and U.S. Patent Applications 20040023261 and 20050107478; light imaging contrast agents such as those described in U.S. Pat. No. 6,540,981; fluorescent dye those described in U.S. Pat. Nos. 6,689,391 and 6,406,856; and mass labels such as those described in U.S. Pat. No. 6,824,981.

Detector Probe: Detector probes are molecules, including oligonucleotides, that can hybridize in a sequence-specific manner to at least a portion of a sequence tag, i.e., at least a portion of a nucleic acid bridge. In one embodiment, a detector probe can be coupled to a sequence tag, wherein the detector probe will not bind to the target nucleic acid portion of a sequence tag. This is so that the target nucleic acid portion of the sequence tag is free to bind to a capture probe. In another embodiment, a detector probe can be coupled to a capture probe-sequence tag hybrid, wherein the detector probe will not bind to the target nucleic acid portion of a sequence tag. In another embodiment, a detector probe can hybridize in a sequence-specific manner to a sequence tag comprising complementary sequence to at least a portion of both a bridge portion and a target nucleic acid portion of the sequence tag. In this embodiment, the detector probe can be coupled to a sequence tag in a manner dependent upon sequence in the target nucleic acid portion of a sequence tag. In the disclosed method, detector probes include those employed in facilitating the detection of capture probe-sequence tag hybrids. In some cases, detector probes comprise a label such as fluorescein which may be introduced for direct fluorescence detection, for example. Examples of fluoresceins include TAMRA, 6-FAM, Cy3, Cy5, Fluorescein-dT, HEX, TAMRA-dT, and TET. In other cases, detector probes can comprise a targeting moiety such as biotin or aptamer, for example. In other cases, detector probes can also include one or more photocleavable nucleotides to facilitate release of a portion of the sequence tag and/or a label.

In the disclosed method, various detector probes may be employed, each comprising a single-stranded portion, at least one label or a targeting moiety. These detector probes may have the same or different length, may have the same or different nucleic acid sequence, and may have the same or different label. A detector probe is capable of forming a duplex structure in a sequence-specific manner with a sequence tag. Examples of detector probes include oligonucleotides, hairpin oligonucleotides, partial duplex nucleic acids, and combinations comprising one or more of the foregoing detector probes.

Ligator Probe: Ligator probes are molecules, including oligonucleotides, that can hybridize in a sequence-specific manner to a bridge portion of the sequence tag, forming a duplex structure. In the disclosed method, ligator probes are employed in facilitating production of partial duplex sequence tags. In some cases, ligator probes can also include one or more photocleavable nucleotides to facilitate release of a portion of the sequence tag and/or a label.

In the disclosed method, various ligator probes are described, each comprising a single-stranded portion, at least one label or a targeting moiety, and is capable of forming a duplex structure in a sequence-specific manner with a complementary bridge portion of a sequence tag. Examples of ligator probes include oligonucleotides, hairpin oligonucleotides and partial duplex nucleic acids.

Detector Array: A detector array (also referred to herein as an array) comprises a plurality of capture probes, wherein the plurality of capture probes is immobilized on an addressable support. A detector array may comprise a single type or a mixture of capture probes types, wherein a type can be a partial duplex hairpin, a partial duplex, a oligonucleotide, or a branched oligonucleotide (dendrimer). Various types of capture probes are illustrated in FIGS. 7 and 8.

The array may include a plurality of addressable portions, wherein the capture probe is immobilized at a distinguishable or predetermined address in the array. In this context, plurality of capture probes refers to multiple capture probes each having a different sequence. Each address in the array may comprise one or more types of capture probes. Each address may comprise multiple copies of the capture probe. The spatial separation of capture probes of different and/or same sequence in the array allows separate detection and identification capture probe-sequence tag hybrids. If a capture probe-sequence tag hybrid is detected at a given address in an array, it indicates a labeled detector probe hybridized to capture probe-sequence tag hybrid immobilized at that address in the array. Each address in the array is identifiable.

Capture probes immobilized on planar substrates include spatial separation at identifiable locations (herein referred as a planar address), wherein the capture probes may be of different and/or same sequence. Planar substrates allow separate detection and identification of capture probe-sequence tag hybrids.

Capture probes immobilized on beads include spatial separation in identifiable populations (herein referred as a bead address), wherein a bead may be distinguished by its physical properties such as size, dimension, label, or any combination thereof. Beads allow separate detection and identification of capture probe-sequence tag hybrids.

Capture probes immobilized on polymeric micelles include spatial separation in identifiable populations (herein referred as a micelle address), wherein a bead may be distinguished by its physical properties such as size, dimension, label, or any combination thereof. Polymeric micelles allow separate detection and identification of capture probe-sequence tag hybrids.

Rolling circle amplification target circle: An amplification target circle (ATC) is a circular single-stranded nucleic acid having portions suitable for rolling circle amplification. An ATC may have a length of about 40 to about 100 nucleotides, for example. When amplified, an ATC gives rise to a long nucleic acid molecule containing multiple repeats of sequences complementary to the ATC. This long nucleic acid molecule is referred to as a tandem sequences nucleic acid. The tandem sequences nucleic acid contains sequences complementary to the primer complement portion and reporter portion of the ATC.

Strand displacement amplification (SDA): Strand Displacement Amplification is an isothermal, in vitro method of amplifying DNA. Exponential amplification results from coupling sense and antisense reactions in which strands displaced from a sense reaction serve as target for an antisense reaction and vice versa. Target generation process occurs at a single temperature (after initial heat denaturation of the double-stranded DNA).

Hybridization chain reaction (HCR): Hybridization chain reaction (HCR), in which stable DNA monomers assemble only upon exposure to a target DNA fragment. In the simplest version of this process, two stable species of DNA hairpins coexist in solution until the introduction of initiator strands triggers a cascade of hybridization events that yields nicked double helices analogous to alternating copolymers. The average molecular weight of the HCR products varies inversely with initiator concentration. Amplification of more diverse recognition events can be achieved by coupling HCR to aptamer triggers.

Catalog: A catalog refers to a collection of detector probes from detector arrays, a collection of the presence of detector probes on detector arrays, a collection of capture probes, a collection of sequence tags, a collection of nucleic acid fragments in a sample, or a collection of nucleic acid sequences in a sample. The information in the catalog may be in the form of addressable information (that is, address in the detector array) or, in the form of sequences. Suitable sequence information for catalogs includes sequences of capture probes to which a detector probe was coupled and sequences of nucleic acid fragments present in the sample (derived from the addresses in the detector array where detectors probes were coupled). Catalogs can also contain, or be made up of, other information derived from the information generated in the disclosed method, and can be combined with information obtained or generated from other sources. One of ordinary skill in the art of software engineering can produce a catalog. The informational nature of catalogs produced lends itself to combination and/or analysis using known bioinformatics systems and methods.

Catalog Index: A catalog index refers to a grouping and/or ordering of a Catalog according to the values of certain data. Catalog indexes can be produced using clustering algorithms known in the art such as d2_cluster, PaCE (Parallel Clustering of ESTs), UIcluster, EXCAVATOR(EXpression data Clustering Analysis and VisualizATiOn Resource), suffux arrays, and UniGene, for example. One of ordinary skill in the art of software engineering can produce a catalog index. The informational nature of catalog indexes produced lends itself to combination and/or analysis using known bioinformatics systems and methods.

Classification: Classification may include associating a sequence tag and/or a catalog element with a biological context, a semantic context, or a combination thereof and recording in a classifier database, wherein a biological context and/or a semantic context is referred to herein as a classifier. Examples of biological classifiers are organism, strain, gene, gene family, ortholog, paralog, homolog, regulatory element, exon, introns, and combinations thereof. In another example, a computed pattern from a catalog may produce a sequence tag signature classifier. In yet another example, a computed difference pattern from a catalog in the comparison of a reference and tester nucleic acid sample may produce a differential signature classifier. In yet another example, a catalog index element, computed from a catalog, may produce a catalog index classifier. In yet another example, semantic entity classifiers are computed from literature, and may include events, locations, people, and chemicals, for example. One of ordinary skill in the art of software engineering can produce a classification database. The informational nature of classifier databases produced lends itself to combination and/or analysis using known bioinformatics systems and methods.

Preparation, Capture, Labeling, and Detection of Sequence Tags

The terms "first", "second", and the like, herein do not denote any order, quantity, or importance, but rather are used to distinguish one element from another, and the terms "a" and "an" herein do not denote a limitation of quantity, but rather denote the presence of at least one of the referenced item.

A method of forming a population of nucleic acid sequence tags comprises covalently coupling a first target nucleic acid to a first end of a first nucleic acid bridge and a second target nucleic acid to a second end of the first nucleic acid bridge to form a linear chimeric nucleic acid intermediate, wherein the first nucleic acid bridge is disposed between the first target nucleic acid and the second target nucleic acid; and producing from the linear chimeric nucleic acid intermediate a first sequence tag and a second sequence tag, wherein the first sequence tag comprises at least a portion of the first target nucleic acid and at least a portion of the first nucleic acid bridge, and wherein the second sequence tag comprises at least a portion of the second target nucleic acid and at least a portion of the first nucleic acid bridge, wherein the at least a first portion of the first target nucleic acid comprises a first addressable portion and wherein the at least a first portion of the second target nucleic acid comprises a second addressable portion. In addition to at least a portion of the first or second target nucleic acid, an addressable portion may optionally comprise, for example, a primer binding site.

The first nucleic acid bridge may comprise a binding site for a first primer and a binding site for a second primer. In this embodiment, producing sequence tags comprises amplifying the linear chimeric nucleic acid intermediate in the presence of the first primer, the second primer, or both, to form the first sequence tag, the second sequence tag, or both. Further, prior to producing, the linear chimeric nucleic acid intermediate can be cleaved with a second cleaving agent to produce a shortened linear chimeric nucleic acid intermediate, wherein the second cleaving agent is one that cleaves at two sites, wherein first site is located upstream of the binding site and the second site is downstream of the binding site, wherein each site is disposed greater than one nucleotide offset from its binding site.

Prior to producing the sequence tags, the first nucleic acid bridge may be cleaved with a third cleaving agent. A second nucleic acid bridge may then be covalently coupled to the cleaved ends of the first nucleic acid bridge to form a modified linear chimeric nucleic acid intermediate comprising the second nucleic acid bridge disposed between at least a portion of the first target nucleic acid and at least a portion of the second nucleic acid, wherein the first nucleic acid bridge comprises a cleavage site for the third cleaving agent. Also, prior to producing the sequence tags, the modified linear chimeric nucleic acid intermediate may be cleaved with a fourth cleaving agent to produce a shortened modified linear chimeric nucleic acid intermediate, wherein the fourth cleaving agent is one that cleaves at a site disposed greater than one nucleotide downstream from its binding site.

The first target nucleic acid and the second target nucleic acid may be generated by cleaving a nucleic acid sample with a first cleaving agent. Suitable nucleic acid samples include, for example, a mixture of genomic DNA, a reference cDNA mixture, a tester cDNA mixture, and synthetic nucleic acid duplex mixtures. A cDNA may be synthesized using one or more anchored primers, for example. The nucleic acid sample may be a cDNA sample, wherein the cDNA is synthesized from a RNA sample optionally in the presence of one or more dideoxy nucleoside triphosphates. The types of RNA samples include enriched mRNA, and total RNA, for example. RNA samples may be enriched for low abundance RNAs, or high abundance RNAs may be removed.

Another embodiment of a nucleic acid sample is a second sample produced from the same type of cells as a first nucleic acid sample except that the cells from which the first nucleic acid sample is derived are modification-deficient relative to the cells from which the second nucleic acid sample is derived. Samples may be prepared from organisms as follows: the same type of organism and specie/strain, where samples differ by experimental treatment; the same type of organism, but different species/strains; different types of organisms, the same type of specimen (tissue, culture, etc), where samples differ by experimental treatment, where treatment can be time and/or conditions; the same type of tissue, where tissue samples are from different specimens, and/or different cellular compartments.

In one embodiment, the first cleaving agent produces a population of target nucleic acid fragments comprising sticky ends of known sequence. Suitable first cleaving agents include, for example, Type II restriction enzymes such as those wherein the recognition and cleavage site is of known sequence. In another embodiment, the first cleaving agent produces a population of fragments comprising of a plurality of sticky ends. Suitable first cleaving agents include, for example one or more of the Type II restriction enzymes, for which at least a portion of the recognition sequence is known and a portion of the cleavage site is of known sequence. In another embodiment, the first cleaving agent produces a population of fragments comprising of a plurality of sticky ends. Suitable first cleaving agents include, for example one or more of the Type IIS restriction enzymes, for which the recognition sequence is known. In some embodiments, the first cleaving agent produces a population of fragments comprising a plurality of sticky ends. Suitable first cleaving agents include, for example any one or more of the Type IIS restriction enzymes, Type IIB restriction enzymes, or Type III restriction enzymes, for which at least a portion of the recognition sequence is known.

It may be desirable in some cases to remove and/or deactivate a subset of first and/or second target nucleic acids. Prior to forming linear chimeric nucleic acid intermediates, first and/or second target nucleic acids may be reacted with a reagent suitable to reduce the reactivity of a subset of first and/or second target nucleic acids. A suitable reagent may comprise an attachment moiety, for example biotin. The reagent may be, for example, a nucleic acid capable of forming a duplex structure with a single stranded overhang of the first and/or second target nucleic acid, a nucleic acid capable of forming a hairpin at an end of the first and/or second nucleic acid, a nucleic acid capable of forming a hairpin at both ends of the first or the second target nucleic acid, or a combination comprising one or more of the foregoing reagents. Prior to amplifying, the linear chimeric nucleic acid intermediate may optionally be divided into N samples, and wherein amplifying comprises amplifying each of the N samples in the presence of the first primer and the second primer to form the first sequence tag and the second sequence tag.

A cleaving agent may be a restriction enzyme that is insensitive and/or sensitive to modification of its recognition site. Such modifications include methylation, alkylation, dimerization, derivatization, depurination, or ADP-ribosylation.

FIG. 1 illustrates one embodiment of formation of a nucleic acid sequence tag wherein the first nucleic acid bridge comprises two primer-binding sites (i.e., Primer-A and Primer-B) and two Type IIS restriction enzyme recognition sites (i.e., TIIS-A and TIIS-B). The first nucleic acid bridge may be covalently coupled to the first and second target nucleic acids using, for example, DNA ligase, to form a linear chimeric nucleic acid intermediate. To facilitate ligation, the ends of the nucleic acid bridge and the ends of the first and second target nucleic acid may have compatible sticky ends generated, for example, by digestion with a Type II restriction enzyme. In this embodiment, once the linear chimeric nucleic acid intermediate is formed, the ends, which comprise at least a portion of the first and second target nucleic acid, may optionally be cleaved with a second cleaving agent producing a shortened linear chimeric nucleic acid intermediate, wherein the second cleaving agent is one that cleaves at a site disposed greater than one nucleotide offset from its recognition site in the bridge portion. This cleavage may, for example be performed with a Type IIS enzyme, to produce a first and second addressable portion having a length of 2 to 30 nucleotides and thus to reduce the complexity of the sequence tags that are produced. Furthermore the mixture of shortened linear chimeric nucleic acid intermediates may comprise linear chimeric nucleic acid molecules of equal length.

It may be desirable in some cases to remove and/or deactivate the excess or uncoupled nucleic acid bridge. Prior to producing the sequence tags, excess first nucleic acid bridge may be reacted with a reagent suitable to reduce the reactivity of the excess first nucleic acid bridge. Optionally, the bridge may be denatured prior to reacting. Preferably, the suitable reagent will comprise an attachment moiety, for example biotin. The reagent may be, for example, a nucleic acid capable of forming a duplex structure with a single stranded overhang of the first nucleic acid bridge, a nucleic acid capable of forming a hairpin at an end of the first nucleic acid bridge, or a combination comprising one or more of the foregoing reagents.

The first and second sequence tags are produced from the linear chimeric nucleic acid intermediate. In one embodiment, the first and second sequence tags are produced by amplifying the chimeric nucleic acid intermediate in the presence of the first primer and the second primer to form the first sequence tag and the second sequence tag. The first and second primers may optionally comprise an attachment moiety such as biotin. In this embodiment, the first sequence tag comprises, in linear order, a portion of the first target nucleic acid, a Type IIS recognition site, and two primer binding sites. The second sequence tag comprises, in linear order, a portion of the second target nucleic acid, a Type IIS recognition site, and two primer binding sites. The sequence tags can be produced by amplifying the chimeric nucleic acid intermediate or modified nucleic acid intermediate with the first primer, the second primer, or both. Amplification is performed by methods known in the art such as polymerase chain reaction (PCR), strand displacement amplification (SDA), and hybridization chain reaction (HCA), for example. Double-stranded or single-stranded sequence tags may be obtained.

FIG. 2 illustrates another embodiment of the formation of nucleic acid sequence tags. In this embodiment, the first nucleic acid bridge comprises one or more Type III (or a functionally similar Type II) enzyme recognition sites and the second nucleic acid bridge comprises two primer binding sites (i.e., Primer-A and Primer-B). The first nucleic acid bridge may be covalently coupled to the first and second target nucleic acids using, for example, DNA ligase, to form a linear chimeric nucleic acid intermediate. To facilitate ligation, the ends of the nucleic acid bridge and the ends of the first and second target nucleic acid may have compatible sticky ends generated, for example, by digestion with a restriction enzyme. In this embodiment, the first nucleic acid bridge may optionally be cleaved with a second cleaving agent producing a shortened linear chimeric nucleic acid intermediate, wherein the second cleaving agent is one that cleaves at two sites, one on each side of the cleaving agent, disposed greater than one nucleotide from its binding outside the bridge. This cleavage may, for example be performed with a Type III enzyme, to produce a first and second addressable portion having a length of 2 to 30 nucleotides and thus reducing the complexity of the sequence tags that are produced. Furthermore the mixture of shortened linear chimeric nucleic acid intermediates may comprise linear chimeric nucleic acid intermediate molecules of equal length.

In this embodiment, once the shortened linear chimeric nucleic acid intermediate is formed, the shortened linear chimeric nucleic acid intermediate may be cleaved with a third cleaving agent to produce two fragments each of which contains a portion of a target nucleic acid and a portion of the first nucleic acid bridge. A second nucleic acid bridge, which has complementary ends to the two fragments, may then be ligated to the two fragments to produce a modified chimeric nucleic acid intermediate. It may be desirable in some cases to remove and/or deactivate the excess or uncoupled first and/or second nucleic acid bridge as described previously.

The first and second sequence tags are produced from the modified chimeric nucleic acid intermediate. In one embodiment, the first and second sequence tags are produced by amplifying the modified chimeric nucleic acid intermediate in the presence of the first primer and the second primer to form the first sequence tag and the second sequence tag. In this embodiment, the first sequence tag comprises, in linear order, a portion of the first target nucleic acid, a Type III (or a functionally similar Type II) recognition site, and two primer binding sites. The second sequence tag comprises, in linear order, a portion of the second target nucleic acid, a Type III (or a functionally similar Type II) recognition site, and two primer binding sites. Amplification is performed as described previously.

In some embodiments, the propensity of the chimeric nucleic acid intermediate to concatenate can be reduced (FIG. 3). In this embodiment, partial duplex and/or hairpin structures optionally comprising attachment moieties can be coupled to the end of target nucleic acid fragments with compatible sticky ends to prevent chimeric nucleic acid intermediate polymerization. Bridge coupling and amplification can proceed as described previously.

In yet another embodiment, target fragments having a variety of sticky ends can be employed (FIG. 3 and FIG. 4). Partial duplexes and/or hairpin molecules comprising a region of complementarity to the first or second sequence tag can be coupled to different ends of the target fragments. In this embodiment, the partial duplexes and/or hairpin molecules couple to different ends of the target nucleic acids with compatible sticky ends, thereby selectively inhibiting a subset of target nucleic acids ends from coupling to a first nucleic acid bridge.

In one embodiment, a sequence tag's addressable portion comprises a variable portion (i.e., a portion that is unique to the particular sequence tag). A complement address portion may also be referred to as cAddress. In another embodiment, the addressable portion comprises a constant portion (i.e., a portion that is shared by a subset of sequence tags) and a variable portion (i.e., a portion that is unique to the particular sequence tag). The constant portion of the addressable portion may also be referred to herein as a complement probe constant sequence (cPCS). A variable addressable portion may also be referred to as cAddress. Sequence tags are illustrated, for example, in FIGS. 9 and 10.

In some embodiments, a first population of sequence tags may be combined with a second population of sequence tags to form a modified population of sequence tags.

Typically, single stranded sequence tags are produced. In some cases, it may be desirable to selectively deactivate the first single-stranded sequence tags or the second single-stranded sequence tags. In one embodiment, the first single-stranded sequence tag or the second single-stranded sequence tag is hybridized with a nucleic acid capable of forming a duplex structure with the first or second single-stranded sequence tag. The hybrid molecule formed may then be removed from the mixture, for example, via an attachment moiety such as biotin on the nucleic acid capable of forming a duplex structure (FIG. 5). Optionally, the nucleic acid capable of forming a duplex structure is coupled to the first or second single-stranded sequence tag by ligation.

In another embodiment, the bridge portion of a single-stranded sequence tag may optionally comprise a sequence capable of forming a hairpin producing a sequence tag having a partial duplex at an end, herein referred as hairpin sequence tags. In this embodiment, a detector probe may be coupled to the hairpin sequence, wherein the detector probe may comprise a label, a targeting moiety, or combination thereof. The coupling of the detector probe allows the tagging of the single-stranded sequence tag for further study.

In some cases, sequence tags are double stranded when they are produced. It may be desirable to produce single-stranded sequence tags from double-stranded sequence tags. In one embodiment, the first single-stranded sequence tag, the second single-stranded sequence tag or both is produced by hybridizing a nucleic acid capable of forming a duplex structure with one strand of the first sequence tag, the second sequence tag, or both, and removing the hybridized nucleic acid capable of forming a duplex structure with the first sequence tag, the second sequence tag, or both. The nucleic acid comprising a region of complementarity with the first sequence tag, the second sequence tag, or both may be, form example, a biotinylated hairpin nucleic acid. In another embodiment, a nucleic acid comprising a region of complementarity to a sequence tag is coupled by ligation.

In another embodiment, single stranded sequence tags may be hybridized to a ligator probe (FIG. 6). The ligator probe can serve to reduce potential interaction of sequence tags sharing the same bridge portion allowing favorable reaction conditions in subsequence steps of the method. In addition, hybridized ligator probes can provide two points of hybridization and/or ligation and can enhance hybridization by providing base stacking interactions. The ligator probes include linear probes, PNA probes, and hairpin probe, for example. A double-stranded ligator probe may be employed to produce a partial duplex sequence tag. In another embodiment, double stranded sequence tags can be denatured and then hybridized with the ligator probe (FIG. 6). The ligator probe can serve to keep the two strands of the sequence tag separate.

The sequence tags can be analyzed in a variety of ways. For example, the sequence tags can be amplified, detected, quantified, identified, sequenced, cataloged, classified or a combination comprising one or more of the foregoing. The sequence tags can be detected by determining, directly or indirectly, the presence, amount, presence and amount, or absence of one or more sequence tags. Numerous techniques and methods are known for the analysis of nucleic acid fragments which are suitable for analysis of sequence tags.

In one embodiment, a population of capture probes is hybridized to the nucleic acid sequence tags to form a population of capture probe-sequence tag hybrids (FIGS. 7-10). In some cases, the capture probe may contain a variable address (i.e., Address), which is complementary to an addressable portion of the nucleic acid sequence tags. In other cases, the capture probe may contain a variable address (Address) and a probe constant sequence (PCS) which are complementary to the complement address (cAddress) and the complement probe constant sequence (cPCS) of the nucleic acid sequence tags. A population of capture probes may comprise the same probe capture sequence. The variable address portion may be adjacent the constant sequence portion. The constant sequence portion may be adjacent an attachment moiety on a capture probe. Suitable capture probes include, for example, single-stranded capture probes, hairpin capture probes, branched capture probes, partial duplex capture probes, PNA capture probes, dendrimeric capture probes, or a combination comprising one or more of the foregoing capture probes. The capture probe may be immobilized on a support such as, for example, a surface. In this embodiment, each capture probe may be attached to a unique position (i.e., location) on the solid support. In another embodiment, the capture probe may be attached to a micro-particle, for example, addressable microspheres such as those available from Luminex and encoded glass particles such as those available from CyVera, a division of Illumina, Inc. In yet another embodiment, the capture probe may be attached to an addressable population of polymeric micelles such described in U.S. Pat. No. 6,872,450 and U.S. Patent Application 20050107478.

The capture probe may be coupled to a bead such as a labeled bead. Labeled beads may comprise, for example, a molecular barcode, a mass label, a dye, a fluorophore or semiconductor nanocrystals. The labeled beads may be separated via the label.

Once the capture probe-sequence tag hybrids are formed, the sequence tags may then be detected using detector probes (FIGS. 11 and 12). A detector probe is a nucleic acid molecule capable of hybridizing and ligating to the capture probe-sequence tag hybrids and having a covalently attached label molecule. The detector probe, for example, hybridizes and ligates to a portion of a single-stranded sequence tag that is not hybridized to a capture probe. A terminal end of a population of first labeled detector probes may be coupled to a terminal end of a first population of capture probe-sequence probe hybrids. A detector probe may thus hybridize to a bridge portion site on the sequence tag in the capture probe-sequence tag hybrid. The detector probes may be, for example, linear detector probes, hairpin detector probes, or a combination comprising one or more of the foregoing detector probes. The detector probes may hybridize and ligate to a terminal end of the capture probe-sequence tag hybrid, i.e., an end of the hybrid that is not attached to a support, a bead, or a polymeric micelle In many cases, stacking hybridization occurs when a capture probe hybridizes to a nucleic acid sequence tag to form a population of capture probe-sequence tag hybrids, when a detector probe hybridizes to form a duplex structure with a portion of capture probe-sequence tag hybrids, when a detector probe hybridizes to form a duplex structure with a portion of single-stranded portion of a sequence tag, when a ligator probe hybridizes to form a duplex structure with a portion of single-stranded portion of a sequence tag, or a combination thereof.

The labels may be directly detectable labels such as, for example, fluorescent dyes such as those available from Invitrogen-Molecular Probes, molecular beacons such as those available from SYNTHEGEN, non-fluorescent quenching labels such as those available from Nanogen-Epoch Biosciences, semiconductor nanocrystals labels such as Quantum Dots available from Evident Technologies and amplifiable labels such as rolling circle amplification (RCA) from Amersham Biosciences and labeled antibodies. The labels may also be indirectly detectable labels such as, for example, fluorescent labels, mass spec labels, Quantum Dots, or a combination comprising one or more of the foregoing labels. Combinations of labels and/or detector probes are possible, for example, two detector probes comprising the same or a different label may be employed. The label may be a molecular barcode.

The detector probe may be a labeled single strand, a labeled partial duplex, a labeled hairpin, or a combination comprising one or more of the foregoing. One, two, three or more populations of detector probes may hybridize and ligate to one, two, three or more populations of capture probe-sequence tag hybrids. A first terminal end of the first detector probe may be coupled to a terminal end of the third detector probe, and a second terminal end of the first detector probe may be coupled to a terminal end of the capture probe. A terminal end of the second detector probe may be coupled to a terminal end of the capture probe. A terminal end of the second detector probe may be coupled to a terminal end of the third detector probe.

The populations of detector probes may comprise the same or different labels. FIG. 11 illustrates different hybridization and ligation arrangements of various detector probes on a pair of capture probe-sequence tag hybrids. For example, a single detector probe, at least a portion of which is complementary to the complement address (cAddress) of the sequence tag, may be employed. In another embodiment, a single detector probe which comprises no sequences complementary to the complement address (cAddress) of the sequence tag may be employed. In another embodiment, the detector probe is a hairpin detector probe which may contain an attachment and/or a targeting moiety in addition to, or instead of, a label.

In other embodiments (FIGS. 11-18), combinations of single strand and hairpin detector probes may be employed. For example, two single strand detector probes comprising the same or a different label may be employed. In another embodiment, two labeled single stranded and one hairpin detector probe comprising the same or a different label may be employed. In yet another embodiment, one labeled single stranded and one hairpin detector probe comprising the same or a different label may be employed. Additional detector probe schemes are illustrated in FIGS. 13-18.

In another embodiment, partial duplex sequence tags may be formed from a single stranded sequence tag or a double stranded sequence tag (whereby first denaturing the double-stranded sequence tags) in the presence of a double-stranded ligator probe, and forming a partial duplex sequence tag comprising a ligator probe strand and a sequence tag strand (FIGS. 6 and 6b). One advantage of this embodiment employing double stranded sequence tags is that a pair of target sequences is generated from a single sequence tag thus allowing for parallel assay. Detection methods using partial duplex sequence tags are illustrated in FIG. 12 and are similar to those described above.

In another embodiment, partial duplex sequence tags may be formed from a single stranded sequence tag or a double stranded sequence tag (whereby first denaturing the double-stranded sequence tags) in the presence of a hairpin ligator probe, and forming partial duplex sequence tags comprising a hairpin ligator probe strand and a sequence tag strand (FIG. 6).

In another embodiment, a population of sequence tags may be hybridized to a detector array, wherein the detector array comprises a plurality of capture probes disposed on a substrate or bound to a polymeric micelle. The hybridized sequence tags may then be covalently coupled to a population of detector probes, wherein the population of sequence tags comprises a plurality of sequences. Coupling of the sequence tags to the detector array may then be detected, for example by coupling a plurality of detector probes to a detector array. The detector probes may have the same or different lengths. In this embodiment, the sequence tags may optionally be single-stranded sequence tags. Detecting coupling of the sequence tags may comprise, for example, performing rolling circle replication of an amplification target circle, and wherein replication is primed by the plurality of detector probes. The detector probes may be the same length, and the portion of the detector probes not attached to the array may be the same or different.

Prior to coupling, the population of sequence tags may be combined with a second population of sequence tags to form a modified population of sequence tags. A reference population sequence tags may optionally be combined with the modified population of sequence tags. Also, prior to coupling, the sequence tags may be contacted with a reagent suitable to produce a population of sequence tags having reduced reactivity. A population of sequence tags having reduced reactivity may be separated from a remaining population of sequence tags. In addition, the population of sequence tags may comprise a catalog of sequence tags for a nucleic acid sample.

Signal Processing

The presence, absence, and/or quantity of a sequence tag can be determined by signal processing methods known in the art. One suitable signal processing method includes Quantum Resonance Interferometry as described in U.S. Pat. No. 6,671,625. The sequence of at least a portion of the first or second target nucleic acid may be identified using standard sequencing techniques.

Analysis

Once the sequence tags have been detected, there are many ways of analyzing the data, such as, calculating the expression levels and the expression ratios of a sequence tag; identifying sequence tags that have similar expression ratios; grouping the sequence tags that have similar expression ratios in sequence tag pairs, to generate a list of correlated sequence tags (putative set of sequence tags that are of the sample nucleic acid molecule); ordering sequence tag in the list of correlated sequence tags according to expression level of the sequence tags; and fitting the values of the expression levels to a standard curve based on an inverse exponential function.

Identifying correlated sequence tags using a different cDNA sample, wherein the cDNA is synthesized in the presence of a different concentration of the one or more dideoxy nucleoside triphosphates or a different set of one or more dideoxy nucleoside triphosphates, correlating changes in expression of each list of correlated sequence tags with the predicted slope changes predicted by the inverse exponential function corresponding to each of the dideoxy terminator levels, and predicting the order and position within the cDNA of each list of sequence tags.

The information generated from a population of sequence tags may be used, for example, to design a diagnostic assay, to determine biomarkers, to determine bio-signatures; to design primers for nucleic acid samples; to determine information about the sequence tags; and the like. The amounts of the sequence tags may be normalized by employing a sequence tag mimic along with the nucleic acid sample. Also, differential expression analysis may be employed. The presence and levels of different sequence tags in different samples may be compared. Relative levels among the same sequence tags produced from different nucleic acid samples may be compared, wherein one nucleic acid sample exhibits restriction enzyme sensitivity in the method. The differences in the patterns indicate modification.

Cataloging

Recording in a database the sequence tag includes: sequence tag composition, target nucleic acid portion composition, length, parent nucleic acid sample and its producing history details, producing sequence tag history details.

Capture probes of different sequence can be immobilized at different addresses on a detector array, wherein an address is a location on a substrate, distinguishable bead population, or a distinguishable polymeric micelle population. In this way, the sequence of the addressable portion of the capture probe-sequence tag hybrid can be determined by which address having detected signal provided by the label bound to the detector probes. A detector array is used in determining the presence, amount, or absence of detector probes at different addresses, thus proportional to the presence, amount, or absence of sequence tags. The presence, amount, or absence of target nucleic acid sequence, is determined by a computed sequence. For this reason, cataloging the signals (that is, the presence, amount, presence and amount, or absence of detector probes), the detector probe sequences, and the sequence tag producing history details may be performed. Furthermore, the probability of probe mismatch can be used to create more complex catalogs based on differential hybridization of particular addressable portions of sequence tags to different capture probes.

In one embodiment, a catalog from an array of detector arrays can be used to compute a pattern of signals that provides a signature or fingerprint of target nucleic acids from a nucleic acid sample.

Catalogs of nucleic acid samples can be compared to a similar catalog derived from another sample to detect similarities and differences in the samples (which is indicative of similarities and differences in the nucleic acids in the samples). For example, a catalog of a first nucleic acid sample can be compared to a catalog of a sample from the same type of organism as the first nucleic acid sample, a sample from the same type of tissue as the first nucleic acid sample, a sample from the same organism as the first nucleic acid sample, a sample obtained from the same source but at time different from that of the first nucleic acid sample, a sample from an organism different from that of the first nucleic acid sample, a sample from a type of tissue different from that of the first nucleic acid sample, a sample from a strain of organism different from that of the first nucleic acid sample, a sample from a species of organism different from that of the first nucleic acid sample, or a sample from a type of organism different from that of the first nucleic acid sample.

The same type of tissue is tissue of the same type such as liver tissue, muscle tissue, or skin (which may be from the same or a different organism or type of organism). The same organism refers to the same individual, animal, or cell. For example, two samples taken from a patient are from the same organism. The same source is similar but broader, referring to samples from, for example, the same organism, the same tissue from the same organism, the same cDNA, or the same cDNA library. Samples from the same source that are to be compared can be collected at different times (thus allowing for potential changes over time to be detected). This is especially useful when the effect of a treatment or change in condition is to be assessed. Samples from the same source that have undergone different treatments can also be collected and compared using the disclosed method. A different organism refers to a different individual organism, such as a different patient, a different individual animal. Different organism includes a different organism of the same type, or organisms of different types. A different type of organism refers to organisms of different types such as a dog and cat, a human and a mouse, or *E. coli* and *Salmonella*, for example. A different type of tissue refers to tissues of different types such as liver and kidney, or skin and brain. A different strain or species of organism refers to organisms differing in their species or strain designation as those terms are understood in the art.

Classification

Many areas in bioinformatics involve class prediction, for example: (1) assigning gene expression patterns or profiles to defined classes, such as tumor and normal classes; (2) recognition of active sites, such as phosphorylation and ATP-binding sites, on proteins; (3) predicting whether a molecule will exhibit biological activity, e.g., in drug discovery, including the screening of databases of small molecules to identify molecules of possible pharmaceutical use; (4) distinguishing exon from intron DNA and RNA sequences, and determining their boundaries; (5) establishing genotype/phenotype correlations, for example to optimize cancer treatment, or to predict clinical outcome or various neuromuscular disorders.

Classification includes classifying genetic conditions, diseases, tumors etc., and/or for predicting genetic diseases, and/or for associating molecular genetic parameters with clinical parameters and/or for identifying tumors by gene expression profiles etc. Classification can include providing molecular genetic data and/or clinical data, optionally automatically generating classification, prediction, association and/or identification data by means of machine learning, and automatically generating (further) classification, prediction, association and/or identification data by means of supervised machine learning.

Classification can be done, for example, based upon structural, regulatory, or gene features such as sequence features. Classification can also be done based upon function using a functional database. Classification can also be done based on structural databases including orthologs, homologs, paralogs, regulatory motifs, alternative splice variants, and the like. Classification can be done based on disease indication databases. Classification can be done based upon databases of agricultural traits. Classification can be done based upon databases of semantic entities.

Other Uses of Sequence Tags

Populations of sequence tags may also be employed as genome probes for locating and mapping exons, or employed as biological markers in biological assays, for example.

Kit

Each kit comprises the reagents to produce a sequence tag comprising a cleaving agent, a first nucleic acid bridge, a detector array comprising a plurality of capture probes, a detector probe, and a means for detecting a presence, an amount, or an absence of binding of the detector probe to the detector array. The kit may optionally comprise a reagent suitable to reduce the reactivity of excess first nucleic acid bridge. The kit may optionally comprise software for cataloging, catalog indexing, and classifying the sequence tags.

Each reagent can be supplied in a solid form or dissolved/suspended in a liquid buffer suitable for inventory storage, and later for exchange or addition into the reaction medium when the test is performed. Suitable packaging can be provided. The kit can optionally provide additional components that are useful in the methods. These optional components include, but are not limited to, buffers, capture probes, labels, reaction surfaces, means for detection, detector probes, control samples, instructions, and interpretive information. The kits can be employed to test a variety of biological samples, including body fluid, solid tissue samples, tissue cultures or cells derived therefrom and the progeny thereof, and sections or smears prepared from any of these sources.

What is claimed is:

1. A method of forming a population of nucleic acid sequence tags,
comprising:
covalently coupling a first linear target nucleic acid having two free ends to a first end of a first nucleic acid bridge and covalently coupling a second linear target nucleic acid having two free ends to a second end of the first nucleic acid bridge to form a linear chimeric nucleic acid intermediate, wherein the first nucleic acid bridge is disposed between the first linear target nucleic acid and the second linear target nucleic acid,
cleaving the linear chimeric nucleic acid intermediate to form a shortened linear chimeric nucleic acid intermediate; and
producing from the shortened linear chimeric nucleic acid intermediate a first sequence tag and a second sequence tag, wherein the first nucleic acid bridge comprises a binding site for a first primer and a binding site for a second primer, and wherein producing comprises amplifying the shortened linear chimeric nucleic acid intermediate in the presence of the first primer, the second primer, or both, to form the first sequence tag, the second sequence tag, or both,
wherein the first sequence tag comprises at least a portion of the first target nucleic acid and at least a portion of the first nucleic acid bridge, and wherein the second sequence tag comprises at least a portion of the second target nucleic acid and at least a portion of the first nucleic acid bridge, wherein the at least a first portion of the first target nucleic acid comprises a first addressable portion and wherein the at least a first portion of the second target nucleic acid comprises a second addressable portion;
wherein the first linear target nucleic acid and the second linear target nucleic acid are not covalently linked until coupling to the nucleic acid bridge, and wherein the first target nucleic acid and the second target nucleic acid are produced from the same nucleic acid sample,
wherein the first nucleic acid bridge comprises 2 restriction endonuclease recognition sequences for endonucleases that cleave at a sequence outside of the nucleic acid bridge, wherein the cleavage sequences are outside of opposite ends of the bridge, wherein the 2 restriction endonuclease recognition sequences are separated by a plurality of nucleotides,
wherein the first sequence tag and the second sequence tag comprise at least a first bridge portion,
wherein the first sequence tag and the second sequence tag are suitable for simultaneous detection without requiring pooling, sorting, or adapter mediated indexing, and wherein the first and second addressable portions have a fixed length of 2 to 30 nucleotides.

2. The method of claim 1, further comprising producing the first target nucleic acid and the second target nucleic acid by cleaving a nucleic acid sample with a first cleaving agent.

3. The method of claim 1, wherein the first nucleic acid bridge comprises a first cleaving agent recognition site and a second cleaving agent recognition site.

4. The method of claim 3, further comprising, prior to producing,
cleaving the linear chimeric nucleic acid intermediate with a second cleaving agent to produce a shortened linear chimeric nucleic acid intermediate, wherein the second cleaving agent is one that cleaves at a site disposed greater than one nucleotide offset from its binding site.

5. The method of claim 1, wherein the first and second sequence tags are single-stranded and wherein the first single-stranded sequence tag, the second single-stranded sequence tag, or both, is isolated by coupling a nucleic acid comprising a region of complementarity with a sequence tag, and removing the coupled duplex structure formed with the first sequence tag, the second sequence tag, or both.

6. The method of claim 1, further comprising detecting, quantifying, amplifying, sequencing, cataloging, classifying, or a combination comprising one or more of the foregoing, the first sequence tag, the second sequence tag, or a combination comprising one or more of the foregoing sequence tags.

7. The method of claim 6, comprising detecting and quantifying the first sequence tag, the second sequence tag, or a combination comprising one or more of the foregoing sequence tags.

8. The method of claim 1, further comprising: coupling a population of capture probes to an end of the population of sequence tags to form a population of capture probe-sequence probe hybrid molecules.

9. The method of claim 8, wherein the capture probe is coupled to the hydrophilic portion of a polymeric micelle.

10. The method of claim 8, further comprising incubating the population of capture probe-sequence probe hybrid molecules with a population of first labeled detector probes, wherein the population of first labeled detector probe is capable of hybridizing to the population of capture probe-sequence probe hybrid molecules.

11. The method of claim 8, further comprising, prior to coupling, contacting the sequence tag with a reagent suitable to produce a population of sequence tags having reduced reactivity.

12. The method of claim 1, wherein the population of sequence tags comprises a catalog of sequence tags for a nucleic acid sample.

13. The method of claim 1, further comprising cataloging the population of sequence tags.

14. The method of claim 1, further comprising classifying the population of sequence tags.

15. The method of claim 1, wherein the population of sequence tags comprises a direct association between a sequence tag and at least one classifier in a classifier database, wherein a classifier database comprises biological classifiers, semantic entity classifiers, sequence tag signature classifier, differential signature classifier, semantic entities classifiers, or a combination comprising one or more of the foregoing classifiers.

16. The method of claim 1, wherein the first addressable portion consists of 2 to 30 nucleotides, and the second addressable portion consists of 2 to 30 nucleotides.

* * * * *

SEQUENCE LISTING

```
<160> NUMBER OF SEQ ID NOS: 1

<210> SEQ ID NO 1
<211> LENGTH: 11
<212> TYPE: DNA
<213> ORGANISM: Artificial Sequence
<220> FEATURE:
<223> OTHER INFORMATION: restriction enzyme recognition sequence
<220> FEATURE:
<221> NAME/KEY: misc_feature
<222> LOCATION: (4)..(4)
<223> OTHER INFORMATION: n = a/c/g/t
<220> FEATURE:
<221> NAME/KEY: misc_feature
<222> LOCATION: (5)..(5)
<223> OTHER INFORMATION: n = a/c/g/t
<220> FEATURE:
<221> NAME/KEY: misc_feature
<222> LOCATION: (6)..(6)
<223> OTHER INFORMATION: n = a/c/g/t
<220> FEATURE:
<221> NAME/KEY: misc_feature
<222> LOCATION: (7)..(7)
<223> OTHER INFORMATION: n = a/c/g/t
<220> FEATURE:
<221> NAME/KEY: misc_feature
<222> LOCATION: (8)..(8)
<223> OTHER INFORMATION: n = a/c/g/t

<400> SEQUENCE: 1
gccnnnnngg c                                                           11
```